United States Patent
Furukawa et al.

(10) Patent No.: US 6,916,944 B2
(45) Date of Patent: Jul. 12, 2005

(54) BISMUTH COMPOUND, PROCESS OF PRODUCING THE SAME, AND PROCESS OF PRODUCING A FILM

(75) Inventors: Taishi Furukawa, Ebina (JP); Noriaki Oshima, Yokohama (JP); Kenichi Sekimoto, Sagamihara (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 10/819,120

(22) Filed: Apr. 7, 2004

(65) Prior Publication Data

US 2004/0204483 A1 Oct. 14, 2004

(30) Foreign Application Priority Data

| Apr. 8, 2003 | (JP) | ................................... P. 2003-104323 |
| Apr. 30, 2003 | (JP) | ................................... P. 2003-125462 |
| Jul. 22, 2003 | (JP) | ................................... P. 2003-199848 |
| Aug. 25, 2003 | (JP) | ................................... P. 2003-208662 |
| Aug. 25, 2003 | (JP) | ................................... P. 2003-208663 |

(51) Int. Cl.[7] .............................. C07F 9/94; C23C 16/00
(52) U.S. Cl. ...................................... 556/70; 427/248.1
(58) Field of Search .......................................... 556/70

(56) References Cited

FOREIGN PATENT DOCUMENTS

JP        5-271940 A     10/1993

OTHER PUBLICATIONS

Hitomi Suzuki et al., "Chiral Chlorobismuthines Stabilized by the Intramolecular Coordination of an N,N–Dimethylamino Group: X–Ray Structure Analysis, Asymmetric Induction at the Bismuth Centre, and Dynamic Behavior in Solution", J. Chem. Soc. Perkin Trans. 1993, pp. 2969–2973.

Primary Examiner—Porfirio Nazario-Gonzalez
(74) Attorney, Agent, or Firm—Sughrue Mion, PLLC

(57) ABSTRACT

A novel bismuth compound having excellent vaporization characteristic and/or thermal stability, a process of producing the same and a process of producing a film in the film formation by the CVD process are disclosed. Bismuth compounds each represented by the following formula 1, 5 and 9, processes of producing the same, and processes of producing a film.

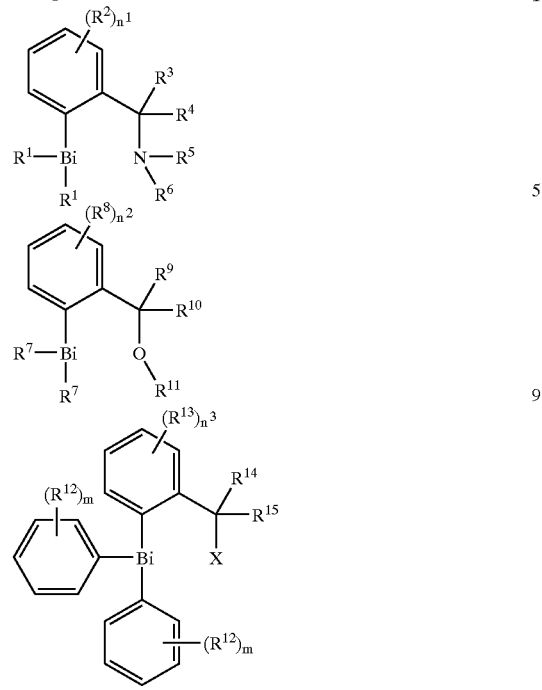

In the formulae, $R^1$ and $R^7$ each represents a lower alkyl group; $R^2$, $R^8$, $R^{12}$, and $R^{13}$ each represents a lower alkyl group, a lower alkoxy group, or the like; m represents the number of the substituent $R^{12}$ in the range of 0–5; $n^1$, $n^2$, and $n^3$ respectively represent the number of the substituent $R^2$, the number of the substituent $R^8$, and the number of the substituent $R^{13}$ each in the range of 0–4; and $R^3$ to $R^6$, $R^9$ to $R^{11}$, $R^{14}$, and $R^{15}$ each represents hydrogen, a lower alkyl group, or the like, provided that specific combinations of the substituents are excluded.

34 Claims, 8 Drawing Sheets

FOREIGN PATENT DOCUMENTS

| | | |
|---|---|---|
| JP | 8-330304 A | 12/1996 |
| JP | 8-339716 A | 12/1996 |

OTHER PUBLICATIONS

The Chemical Society of Japan 1999, vol. 1999, No. 1, pp. 45–48 (with English translation).

Yohsuke Yamamoto et al., "Synthesis and Crystal Structure of Intramolecularly Coordinated Organobismuth Compounds and Edge Inversion at Trivalent Bismuth", J. Am. Chem. Soc. 1992, 114, pp. 7906–7907.

Yohsuke Yamamoto et al., "Experimental Investigation on Edge Invention at Invention at Trivalent Bismuth and Antimony: Great Acceleration by Intra– and Intermolecular Nucleophilic Coordination", J. Am. Chem. Soc. 1995, 117, pp. 3922–3932.

Smuruthi Kamepalli et al., "Synthesis and Structures of Intramolecularly Base–Coordinated Aryl Group 15 Compounds", Inorg. Chem. 1996, 35, pp. 6179–6183.

Claire J. Carmalt et al., "Synthesis and Structures of Intramolecularly Base–Coordinated Group 15 Aryl Halides", Inorg. Chem. 1997, 36, pp. 2770–2776.

Md. Mizanur Rahman et al., "Sodium Diarylbismuthide as a Reagent for the Bismuthanation of Reactive Arenes. Application to the Synthesis of Mixed Triarylbismuthanes Bearing a Substituent Group Incompatible with Grignard and Organolithium Reagents", Organometallics 1997, 16, pp. 3565–3568.

Leo E. Manzer, "Paramagnetic Organometallic Compounds of the Early Transition Metals Stabilized by Chelating Benzyl and Phenyl Ligands", Journal of the American Chemical Society, 1978, pp. 8068–8073.

Derek H.R. Barton et al., "Pentavalent Organobismuth Reagents. Part VI. Comparative Migratory Aptitudes of Aryl Groups in the Arylation of Phenols and Enols by Pentavalent Bismuth Reagents", Pergamon Journals Ltd., 1986, vol. 42, No. 12. pp. 3111–3122.

Henry Gilman et al., "Unsymmetrical Organobismuth Compounds", The Journal of the American Chemical Society, 1941, vol. 63, No. 207, pp. 207–211.

Frederick Challenger, "Organo–derivatives of Bismuth. Part I. The Preparation and Properties of some Tertiary Aromatic Bismuthines and their Halogen Derivatives." J. Chem. Soc., 1914, vol. 105, No. 2210, pp. 2210–2218.

Frederick Challenger et al., "Organo–derivatives of Bismuth. Part II. The Stability of Derivatives of Quinquevalent Bismuth", 1915, vol. 107, No. 16, pp. 16–25.

Henry Gilman et al., "The Conversion of Arylbismuth Halides to Triarylbismuth Compounds", The Journal of the American Chemical Society, 1940, vol. 62, No. 665, pp. 665–666.

Edward W. Abel et al., Silicon Group, Arsenic, Antimony, and Bismuth, Pergamon Press, vol. 2, pp. 321–347.

Sir Geoffrey Wilkinson et al., "The Synthesis, Reactions and Structures of Organometallic Compounds", Pergamon Press, vol. 2, pp. 681–707.

Leon D. Freedman et al., "Preparation, Reactions, and Physical Properties of Organobismuth Compounds", Chem. Rev. 1982, vol. 82, pp. 15–57.

Patent Abstracts of Japan—2000053422 (2000).

Hitomi Suzuki et al.., "Unexpected formation of highly stabilized tetrakis–(2–alkoxyphenyl)bismuthonium salts in the oxidation of tris–(2–alkoxyphenyl)bismuthanes with iodosylbenzene", J. Chem. Soc., Perkin Trans. 1, 1997, pp. 1609–1616.

European Search Report dated Jul. 28, 2004.

BISMUTH COMPOUND, PROCESS OF PRODUCING THE SAME, AND PROCESS OF PRODUCING A FILM

FIELD OF THE PRESENT INVENTION

The present invention relates to a bismuth compound that is useful for forming bismuth-containing thin films by the chemical vapor deposition process (CVD process) or the like and can be stably supplied, a process of producing the same, and a process of producing a film.

DESCRIPTION OF THE RELATED ART

As present, DRAM is mainly used as a semiconductor memory. DRAM electrically stores data, and therefore, when a power source is cut, the stored data are lost. Then, use of FeRAM capable of holding stored data even after cutting a power source is being investigated. Also, it is expected to apply FeRAM to IC cards and the like.

In FeRAM device, a ferroelectric material is used as a capacitor. Since bismuth layer structured ferroelectrics (BLSF) (for example, SBT ($SrBi_2Ta_2O_9$), BIT ($Bi_4Ti_3O_{12}$), BLT ($Bi_{4-x}La_xTi_3O_{12}$), and BNT ($Bi_{4-x}Nd_xTi_3O_{12}$)), and PZT ($PbZr_xTi_{1-x}O_3$) exhibit excellent ferroelectric characteristics, they are eagerly investigated as a candidate material. Of these, since PZT contains lead, it is not desired from the environmental standpoint. Accordingly, BLSF are the likeliest.

As the method of forming such ferroelectric thin films in highly integrated memory, the CVD process is optimum from the standpoints of excellent step coverage property and composition controllability.

Hitherto, triphenylbismuth has been mainly investigated as a bismuth compound in the CVD process. Not only triphenylbismuth is stable in air so that it is easy for handling, but also it exhibits sufficient vaporization characteristic. Accordingly, triphenylbismuth has been used from the first of start of investigation of the film formation of bismuth-containing films by the CVD process. Also, tri(2-tolyl)bismuth and tri(3-tolyl)bismuth as a triaylbismuth compound, tri(tert-butoxy)bismuth and tri(tert-amyloxy)bismuth as a trialkoxybismuth compound, and tri(dipivaloylmethanato)bismuth [Bi(DPM)$_3$] as a tri(β-diketonato)bismuth compound are investigated (for example, see JP-A-5-271940, JP-A-8-330304 and JP-A-8-339716). However, these compounds involve problems in reactivity with water and/or vaporization characteristic. Also, trimethylbismuth is a bismuth compound having good vaporization characteristic and having characteristics suitable for the CVD process. However, since this compound is dangerous for explosion by heating or impact, its handling is very difficult.

A diaryl(2-(N,N-dimethylaminoalkyl)phenyl)bismuth is synthesized in the solution as a reaction intermediate of chiral bismuth compounds but is not insolated yet, and its physical properties have not been clarified yet (see, for example, see *J. Chem. Soc. Perkin Trans.*, 1, 2969 (1993)).

In the CVD process, since it is necessary to supply the precursor of thin films as a gas, a method in which the precursor is gasified by heating a vessel charged with the precursor is widely investigated. However, since triphenylbismuth does not have sufficient thermal stability and causes heat decomposition within the vessel, there is encountered a problem that the concentration of the precursor gas changes so that a constant amount of the precursor cannot be supplied. With respect to this problem, bismuth compounds that are more easily gasified than triphenylbismuth and can be supplied without causing heat decomposition, or bismuth compounds that are superior in thermal stability to triphenylbismuth and have sufficient vaporization characteristic are desired.

As bismuth compounds having excellent vaporization characteristic, trimethylbismuth is known. However, as described previously, trimethylbismuth is dangerous for explosion by heat, and therefore, it cannot be said that this compound is a preferred material. On the other hand, as bismuth compounds attempting to improve thermal stability, tri(2-tolyl)bismuth is known (see, for example, JP-A-5-271940 and *Bulletin of the Chemical Society of Japan*, No. 1, 45 (1999)). However, in tri(2-tolyl)bismuth, there is no remarkable difference between the vaporization temperature and the thermal decomposition temperature so that there is encountered a problem that the temperature control in the film formation is difficult.

For the method of gasification of the precursor in the CVD process, a method of bubbling an inert gas in a liquid precursor or in a solution of a precursor to gasify the precursor (bubbling method), or a method of injecting a solution of a precursor dissolved in a solvent into an inert gas stream to gasify the precursor (injection method) is widely employed. According to the bubbling method, since the precursor is used in the liquid state, a solid precursor must be once melted so that it is difficultly handled. Precursors that are liquid at room temperature are preferable. On the other hand, in the case where the injection method is employed, the precursor must be uniformly dissolved in the solvent, and therefore, liquid precursors are preferable.

SUMMARY OF THE PRESENT INVENTION

One object of the present invention is to provide a novel bismuth compound having excellent vaporization characteristic, a process of producing the same, and a process of producing a film in the film formation by the CVD process. Another object of the present invention is to provide a novel bismuth compound having sufficient vaporization characteristic and excellent thermal stability and a process of producing the same.

Under these circumstances, the present inventors made extensive and intensive investigations. As a result, it has been found that according to the first invention and second invention of this application, the foregoing objects can be achieved by a bismuth compound containing a low molecular weight alkyl group and an aryl group having a substituent having a coordinating ability, leading to accomplishment of the present invention. Also, it has been found that according to the third invention of this application, the foregoing objects can be achieved by a bismuth compound containing a low molecular weight aryl group and an aryl group having a substituent having a coordinating ability, leading to accomplishment of the present invention.

Specifically, the first invention of this application is concerned with a bismuth compound represented by the following formula 1:

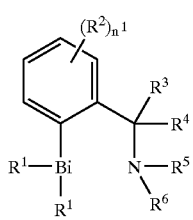

1 wherein $R^1$ represents a lower alkyl group; $R^2$ represents a lower alkyl group, a lower alkoxy group, a lower acyl group, a lower alkoxycarbonyl group, a lower halogenated alkyl group, or a halogen; $n^1$ represents the number of the substituent $R^2$ in the range of from 0 to 4; and $R^3$ to $R^6$ each represents hydrogen, a lower alkyl group, or a lower halogenated alkyl group.

Also, the present invention is concerned with a process of producing the bismuth compound represented by the formula 1, which comprises reacting a monoaryl dihalogenated bismuth represented by the following formula 2:

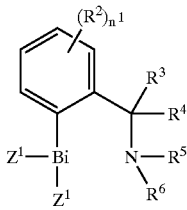

2 wherein $R^2$, $n^1$, and $R^3$ to $R^6$ are the same as defined above; and $Z^1$ represents a halogen, with an $R^1$-converting reagent, wherein $R^1$ is the same as defined above.

Further, the present invention is concerned with a process of producing the bismuth compound represented by the formula 1, which comprises reacting a dialkyl monohalogenated bismuth represented by the following formula 3:

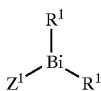

3 wherein $R^1$ and $Z^1$ are the same as defined above, with an arylating reagent represented by the following formula 4:

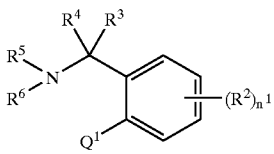

4 wherein $R^2$, $n^1$, and $R^3$ to $R^6$ are the same as defined above; and $Q^1$ represents any of lithium, sodium, potassium, MgCl, MgBr, or MgI.

Also, the present invention is concerned with a process of producing a bismuth-containing film, which comprises subjecting the bismuth compound represented by the formula 1 as a precursor to chemical vapor deposition on a substrate to form a bismuth-containing film.

Also, the second invention of this application is concerned with a bismuth compound represented by the following formula 5:

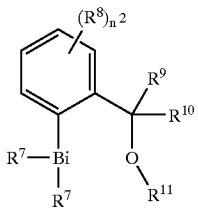

5 wherein $R^7$ represents a lower alkyl group; $R^8$ represents a lower alkyl group, a lower alkoxy group, a lower acyl group, a lower alkoxycarbonyl group, a lower halogenated alkyl group, or a halogen; $n^2$ represents the number of the substituent $R^8$ in the range of from 0 to 4; and $R^9$ to $R^{11}$ each represents hydrogen, a lower alkyl group, or a lower halogenated alkyl group.

Also, the present invention is concerned with a process of producing the bismuth compound represented by the formula 5, which comprises reacting a monoaryl dihalogenated bismuth represented by the following formula 6:

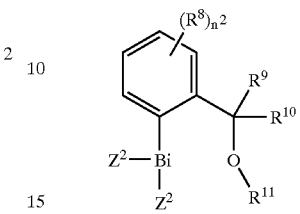

6 wherein $R^8$, $n^2$, and $R^9$ to $R^{11}$ are the same as defined above; and $Z^2$ represents a halogen, with an $R^7$-converting reagent, wherein $R^7$ is the same as defined above.

Further, the present invention is concerned with a process of producing the bismuth compound represented by the formula 5, which comprises reacting a dialkyl monohalogenated bismuth represented by the following formula 7:

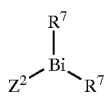

7 wherein $R^7$ and $Z^2$ are the same as defined above, with an arylating reagent represented by the following formula 8:

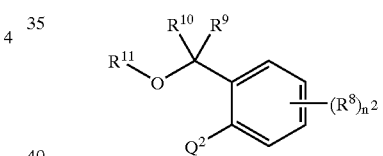

8 wherein $R^8$, $n^2$, and $R^9$ to $R^{11}$ are the same as defined above; and $Q^2$ represents any of lithium, sodium, potassium, MgCl, MgBr, or MgI.

Also, the present invention is concerned with a process of producing a bismuth-containing film, which comprises subjecting the bismuth compound represented by the formula 5 as a precursor to chemical vapor deposition on a substrate to form a bismuth-containing film.

Further, the third invention of this application is concerned with a bismuth compound represented by the following formula 9:

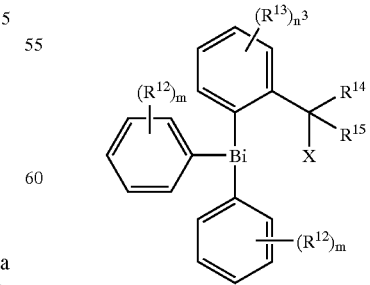

9 wherein $R^{12}$ and $R^{13}$ each represents a lower alkyl group, a lower alkoxy group, a lower acyl group, a lower alkoxycarbonyl group, a lower halogenated alkyl group, or a halogen; m represents the number of the substituent $R^{12}$ in the range of from 0 to 5; $n^3$ represents the number of the substituent $R^{13}$ in the range of from 0 to 4; $R^{14}$ and $R^{15}$ each represents hydrogen, a lower alkyl group, or a lower halogenated alkyl group; and X represents a substituent represented by the following formula 10 or 11:

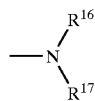

10

11 wherein $R^{16}$ to $R^{18}$ each represents hydrogen, a lower alkyl group, or a lower halogenated alkyl group,
provided that the case (i) where X is represented by the formula 10, $R^{14}$ and $R^{15}$ each represents hydrogen, $R^{16}$ and $R^{17}$ each represents a methyl group, m is 1, $n^3$ is 0, and $R^{12}$ represents a 4-methyl group, a 4-methoxy group, or 4-chloro; and the case (ii) where X is represented by the formula 10, m and $n^3$ are each 0, $R^{15}$ represents hydrogen, $R^{16}$ and $R^{17}$ each represents a methyl group, and $R^{14}$ represents hydrogen or a methyl group are excluded.

Also, the present invention is concerned with a process of producing the bismuth compound represented by the formula 9, which comprises reacting a diaryl monohalogenated bismuth represented by the following formula 12:

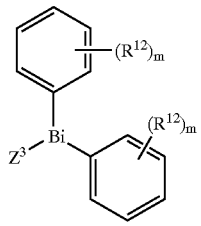

12 wherein $R^{12}$ and m are the same as defined above; and $Z^3$ represents a halogen, with an arylating reagent represented by the following formula 13:

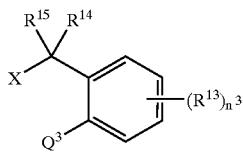

13 wherein $R^{13}$, $R^{14}$, $R^{15}$, $n^3$, and X are the same as defined above; and $Q^3$ represents an alkali metal, MgCl, MgBr, or MgI,
provided that the case (i) where X is represented by the formula 10, $R^{14}$ and $R^{15}$ each represents hydrogen, $R^{16}$ and $R^{17}$ each represents a methyl group, m is 1, $n^3$ is 0, and $R^{12}$ represents a 4-methyl group, a 4-methoxy group, or 4-chloro; and the case (ii) where X is represented by the formula 10, m and $n^3$ are each 0, $R^{15}$ represents hydrogen, $R^{16}$ and $R^{17}$ each represents a methyl group, and $R^{14}$ represents hydrogen or a methyl group are excluded.

Figure 1:
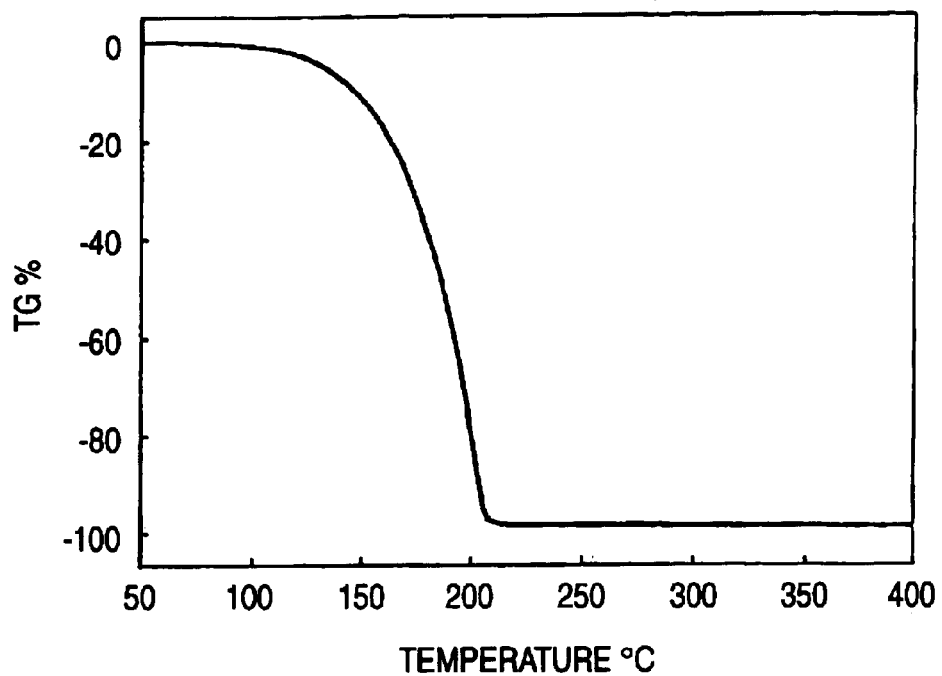
FIG. 1 is a graph showing a TG curve of Example 5.

In the drawings:
1: Vessel
2: Thermostat
3: Reaction chamber
4: Substrate
5: Reaction gas
6: Diluent gas
7: Carrier gas
8: Mass flow controller
9: Mass flow controller
10: Mass flow controller
11: Vacuum pump
12: Exhaust
13: Vessel for bismuth precursor
14: Vessel for titanium precursor
15: Thermostat
16: Thermostat
17: Reaction chamber
18: Substrate
19: Reaction gas
20: Diluent gas
21: Carrier gas
22: Carrier gas
23: Mass flow controller
24: Mass flow controller
25: Mass flow controller
26: Mass flow controller
27: Vacuum pump
28: Exhaust

DETAILED DESCRIPTION OF THE PRESENT INVENTION

The present invention will be described below in more detail.

The term "lower" as referred to in the present specification and claims means one containing a linear, branched or cyclic hydrocarbon group having 1–6 carbon atoms in the group given this term, unless otherwise indicated.

First of all, the first invention and second invention of this application will be described.

In the present invention, $R^1$ represents a lower alkyl group; $R^2$ represents a lower alkyl group, a lower alkoxy group, a lower acyl group, a lower alkoxycarbonyl group, a lower halogenated alkyl group, or a halogen; $n^1$ represents the number of the substituent $R^2$ in the range of 0–4; and $R^3$ to $R^6$ each represents hydrogen, a lower alkyl group, or a lower halogenated alkyl group.

$R^7$ represents a lower alkyl group; $R^8$ represents a lower alkyl group, a lower alkoxy group, a lower acyl group, a lower alkoxycarbonyl group, a lower halogenated alkyl group, or a halogen; $n^2$ represents the number of the substituent $R^8$ in the range of 0–4; and $R^9$ to $R^{11}$ each represents hydrogen, a lower alkyl group, or a lower halogenated alkyl group.

The case where $n^1$ is 3 or less means that hydrogens of the number of $(4-n^1)$ are bound to the aromatic ring. When the compounds of the formula 1 are made hereof by reference, the case where $n^1$ is 0, $R^3$ and $R^4$ each represents hydrogen, and $R^5$ and $R^6$ each represents a methyl group means that a 2-(N,N-dimethylaminomethyl)phenyl group is bound to bismuth; and the case where $n^1$ is 1, $R^2$ represents a methyl group, and $R^3$ to $R^6$ are the same as defined above means that any one of a 2-(N,N-dimethylaminomethyl)-3-tolyl group, a 2-(N,N-dimethylaminomethyl)-4-tolyl group, a 2-(N,N-dimethylaminomethyl)-5-tolyl group, and a 2-(N,N-dimethylaminomethyl)-6-tolyl group is bound to bismuth, respectively. Also, the same is applicable as to $n^2$. That is, when the compounds of the formula 5 are made hereof by reference, the case where $n^2$ is 0, $R^9$ and $R^{10}$ each represents hydrogen, and $R^{11}$ represents a methyl group means that a 2-methoxymethylphenyl group is bound to bismuth; and the case where $n^2$ is 1, $R^8$ represents a methyl group, and $R^9$ to $R^{11}$ are the same as defined above means that any one of a 2-methoxymethyl-3-tolyl group, a 2-methoxymethyl-4-tolyl group, a 2-methoxymethyl-5-tolyl group, and a 2-methoxymethyl-6-tolyl group is bound to bismuth, respectively.

Examples of the lower alkyl group represented by $R^1$ and $R^7$ include a methyl group, an ethyl group, a n-propyl group, an isopropyl group, a n-butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclopropyl group, a cyclobutyl group, a cyclopentyl group, a cyclohexyl group, a cyclopropylmethyl group, a cyclopropylethyl group, and a cyclobutylmethyl group.

Examples of the lower alkyl group represented by $R^2$ and $R^8$ include a methyl group, an ethyl group, a n-propyl group, an isopropyl group, a n-butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclopropyl group, a cyclobutyl group, a cyclopentyl group, a cyclohexyl group, a cyclopropylmethyl group, a cyclopropylethyl group, and a cyclobutylmethyl group.

Examples of the lower alkoxy group represented by $R^2$ and $R^8$ include a methoxy group, an ethoxy group, a propoxy group, an isopropoxy group, a butoxy group, an isobutoxy group, a sec-butoxy group, a tert-butoxy group, a pentyloxy group, a 1-methylbutyloxy group, a 2-methylbutyloxy group, a 3-methylbutyloxy group, a 1,2-dimethylpropyloxy group, a hexyloxy group, a 1-methylpentyloxy group, a 1-ethylpropyloxy group, a 2-methylpentyloxy group, a 3-methylpentyloxy group, a 4-methylpentyloxy group, a 1,2-dimethylbutyloxy group, a 1,3-dimethylbutyloxy group, a 2,3-dimethylbutyloxy group, a 1,1-dimethylbutyloxy group, a 2,2-dimethylbutyloxy group, and a 3,3-dimethylbutyloxy group.

Examples of the lower acyl group represented by $R^2$ and $R^8$ include a formyl group, an acetyl group, a propionyl group, a butyryl group, an isobutyryl group, a valeryl group, a 1-methylpropylcarbonyl group, an isovaleryl group, a pentylcarbonyl group, a 1-methylbutylcarbonyl group, a 2-methylbutylcarbonyl group, a 3-methylbutylcarbonyl group, a 1-ethylpropylcarbonyl group, and a 2-ethylpropylcarbonyl group; examples of the lower alkoxycarbonyl group represented by $R^2$ and $R^8$ include a methoxycarbonyl group, an ethoxycarbonyl group, a propoxycarbonyl group, an isopropoxycarbonyl group, a cyclopropoxycarbonyl group, a butoxycarbonyl group, an isobutoxycarbonyl group, a sec-butoxycarbonyl group, and a tert-butoxycarbonyl group; examples of the lower halogenated alkyl group represented by $R^2$ and $R^8$ include a fluoromethyl group, a difluoromethyl group, and a trifluoromethyl group; and examples of the halogen represented by $R^2$ and $R^8$ include fluorine.

As $R^3$ to $R^6$ and $R^9$ to $R^{11}$, there are enumerated hydrogen; a lower alkyl group (for example, a methyl group, an ethyl group, a n-propyl group, an isopropyl group, a n-butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclopropyl group, a cyclobutyl group, a cyclopentyl group, a cyclohexyl group, a cyclopropylmethyl group, a cyclopropylethyl group, and a cyclobutylmethyl group); and a lower halogenated alkyl group (for example, a fluoromethyl group, a difluoromethyl group, and a trifluoromethyl group).

Although the bismuth compound of the present invention comprising a combination of $R^1$ to $R^6$ or $R^7$ to $R^{11}$ is not particularly limited, specific examples thereof include dimethyl(2-(N,N-dimethylaminomethyl)-4-propylphenyl)bismuth,
diisopropyl(2-(N,N-diethylaminomethyl)-4-propylphenyl)bismuth,
dimethyl(2-(N,N-dimethylaminomethyl)-4-methoxyphenyl)bismuth,
diisopropyl(2-(N,N-diethylaminomethyl)-4-methoxyphenyl)bismuth,
dimethyl(2-methoxymethyl-4-propylphenyl)bismuth,
diisopropyl(2-methoxymethyl-4-propylphenyl)bismuth,
dimethyl(2-methoxymethyl-4-methoxyphenyl)bismuth, and
diisopropyl(2-methoxymethyl-4-methoxyphenyl)bismuth.

It is preferable from the standpoint of lowering the vaporization temperature of the bismuth compound that $R^1$ represents a methyl group, $R^2$ represents an alkyl group having 1–2 carbon atoms, $R^3$ and $R^4$ each represents hydrogen or an alkyl group having 1–2 carbon atoms, and $R^5$ and $R^6$ each represents an alkyl group having 1–2 carbon atoms. Also, it is preferable that $R^7$ represents a methyl group, $R^8$ represents an alkyl group having 1–2 carbon atoms, $R^9$ and $R^{10}$ each represents hydrogen or an alkyl group having 1–2 carbon atoms, and $R^{11}$ represents an alkyl group having 1–2 carbon atoms. It is further preferable that $R^1$ represents a methyl group, $R^2$ represents an alkyl group having 1–2 carbon atoms, $R^3$ and $R^4$ each represents hydrogen or an alkyl group having 1–2 carbon atoms, $R^5$ and $R^6$ each represents an alkyl group having from 1 to 2 carbon atoms, $n^1$ is 0–2, $R^7$ represents a methyl group, $R^8$ represents an alkyl group having 1–2 carbon atoms, $R^9$ and $R^{10}$ each represents hydrogen or an alkyl group having 1–2 carbon atoms, $R^{11}$ represents an alkyl group having 1–2 carbon atoms, and $n^2$ is 0–2.

Although such bismuth compounds are not particularly limited, examples thereof include dimethyl(2-(N,N-dimethylaminomethyl)phenyl)bismuth,
dimethyl(2-(N-ethyl-N-methylaminomethyl)phenyl) bismuth,
dimethyl(2-(N,N-diethylaminomethyl)phenyl)bismuth,
dimethyl(2-(1-(N,N-dimethylamino)ethyl)phenyl)bismuth,
dimethyl(2-(1-(N,N-diethylamino)ethyl)phenyl)bismuth,
dimethyl(2-(1-(N,N-dimethylamino)-1-methylethyl)phenyl) bismuth,
dimethyl(2-(1-(N,N-diethylamino)-1-methylethyl)phenyl) bismuth,
dimethyl(2-(N,N-dimethylaminomethyl)-3-tolyl)bismuth,
dimethyl(2-(N,N-dimethylaminomethyl)-4-tolyl)bismuth,
dimethyl(2-(N,N-dimethylaminomethyl)-5-tolyl)bismuth, and
dimethyl(2-(N,N-dimethylaminomethyl)-6-tolyl)bismuth.

There are further enumerated dimethyl(2-methoxymethylphenyl)bismuth, dimethyl(2-ethoxymethylphenyl)bismuth, dimethyl(2-(1-methoxyethyl)phenyl)bismuth,
dimethyl(2-(1-ethoxyethyl)phenyl)bismuth,
dimethyl(2-(1-methoxy-1-methylethyl)phenyl)bismuth,
dimethyl(2-methoxymethyl-3-tolyl)bismuth,
dimethyl(2-methoxymethyl-4-tolyl)bismuth,
dimethyl(2-methoxymethyl-5-tolyl)bismuth,
dimethyl(2-methoxymethyl-6-tolyl)bismuth,
dimethyl(2-ethoxymethyl-3-tolyl)bismuth, dimethyl(2-ethoxymethyl-4-tolyl)bismuth,
dimethyl(2-ethoxymethyl-5-tolyl)bismuth, and
dimethyl(2-ethoxymethyl-6-tolyl)bismuth.

Of these, dimethyl(2-(N,N-dimethylaminomethyl) phenyl)bismuth and dimethyl(2-methoxymethylphenyl) bismuth are more preferable.

The bismuth compound represented by the formula 1 according to the present invention can be produced by mixing and reacting a monoaryl dihalogeated bismuth represented by the formula 2 with an $R^1$-converting reagent in a solvent, or by mixing and reacting a dialkyl monohalogeated bismuth represented by the formula 3 with an arylating reagent represented by the formula 4 in a solvent.

The bismuth compound represented by the formula 5 according to the present invention can be produced by mixing and reacting a monoaryl dihalogeated bismuth represented by the formula 6 with an $R^7$-converting reagent in a solvent, or by mixing and reacting a dialkyl monohalogeated bismuth represented by the formula 7 with an arylating reagent represented by the formula 8 in a solvent.

The monoaryl dihalogenated bismuth represented by the formula 2 or 6 can be synthesized by, for example, mixing a triaryl bismuth and a trihalogenated bismuth in a proportion of ½ (by mole) in a solvent (*Inorg. Chem.*, 107, 2770 (1997)). In the monoaryl dihalogenated bismuth represented by the formula 2 or 6, $Z^1$ and $Z^2$ each represents a halogen, examples of which include chlorine, bromine, and iodine.

In the arylating reagent represented by the formula 4 or 8, $Q^1$ and $Q^2$ each represents an alkali metal such as lithium, sodium, and potassium, or MgBr, MgCl, or MgI.

$R^2$ to $R^6$, $R^8$ to $R^{11}$, $n^1$, and $n^2$ are the same as defined above. In particular, it is preferable that $R^2$ represents an alkyl group having 1–2 carbon atoms, $R^3$ and $R^4$ each represents hydrogen or an alkyl group having 1–2 carbon atoms, $R^5$ and $R^6$ each represents an alkyl group having 1–2 carbon atoms, $R^8$ represents an alkyl group having 1–2 carbon atoms, $R^9$ and $R^{10}$ each represents hydrogen or an alkyl group having 1–2 carbon atoms, and $R^{11}$ represents an alkyl group having 1–2 carbon atoms. Above all, it is further preferable that $R^3$ and $R^4$ each represents hydrogen, $R^5$ and $R^6$ each represents a methyl group, $R^9$ and $R^{10}$ each represents hydrogen, $R^{11}$ represents a methyl group, $Z^1$ and $Z^2$ each represents chlorine, and $n^1$ and $n^2$ are each 0.

With respect to the $R^1$-converting reagent and $R^7$-converting reagent to be used (wherein $R^1$ and $R^7$ each represents a lower alkyl group), so far as a compound can subject the monoaryl dihalogenated bismuth represented by the formula 2 or 6 to $R^1$-conversion or $R^7$-conversion, respectively, that is, lower alkylation, it is not particularly limited. Examples thereof include a lower alkyl lithium, a lower alkyl sodium, a lower alkyl potassium, a lower alkyl magnesium chloride, a lower alkyl magnesium bromide, and a lower alkyl magnesium iodide. In particular, $R^1$ and $R^7$ are each preferably a methyl group, and the $R^1$-converting reagent and $R^7$-converting reagent are each especially preferably methyl magnesium bromide.

In the synthesis using the monoaryl dihalogenated bismuth represented by the formula 2 and the $R^1$-converting reagent, when the amount of the $R^1$-converting reagent is in excess, a trialkyl bismuth is likely formed, thereby reducing the yield. Therefore, it is preferred to use the $R^1$-converting reagent in an amount of from 1.8 to 2.2 times by mole against the monoaryl dihalogenated bismuth. In mixing these compounds, the $R^1$-converting reagent may be dropped in a solution or suspension of the monoaryl dihalogenated bismuth, or a solution or suspension of the monoaryl dihalogenated bismuth may be dropped in the $R^1$-converting reagent. In the synthesis using the monoaryl dihalogenated bismuth represented by the formula 6 and the $R^7$-converting reagent, the same is applicable. It is preferred to use the $R^7$-converting reagent in an amount of 1.8–2.2 times by mole against the monoaryl dihalogenated bismuth; and the $R^7$-converting reagent may be dropped in a solution or suspension of the monoaryl dihalogenated bismuth, or a solution or suspension of the monoaryl dihalogenated bismuth may be dropped in the $R^7$-converting reagent.

As the solvent, those which are liquid at −80° C. are preferable but are not particularly limited. Preferred examples thereof include diethyl ether, THF, toluene, and hexane. The solvent may be used alone or as mixtures. The solvent to be used in the solution or suspension of the monoaryl dihalogenated bismuth and the solvent used in the $R^1$-converting reagent or $R^7$-converting reagent are not necessarily required to be identical with each other but may be different from each other. With respect to the reaction temperature, the reaction rate is slow at low temperatures, and a trialkyl bismuth may possibly be formed at high temperatures. Accordingly, it is preferable that dropping and mixing are carried out at from −80 to 30° C. and that the temperature is gradually raised to 0° C. to the refluxing temperature of the solvent in such a manner that the reaction temperature becomes the dropping temperature or higher. After the reaction, the reaction mixture is quenched with water or the like, and the desired bismuth compound of the present invention can be recovered from an oily layer. Since the oily layer contains by-products formed by the reaction or quenching in addition to the desired bismuth compound, the oily layer is purified by chromatography, distillation or the like, thereby obtaining the desired bismuth compound of the present invention.

It is possible to produce a bismuth-containing film using the bismuth compound of the present invention as a precursor. In the case where a bismuth-containing film is produced on a substrate by the CVD process using the bismuth compound of the present invention as a precursor, the bismuth compound of the present invention is gasified and then supplied onto the substrate. Examples of the method of gasifying the bismuth compound include a method in which an inert carrier gas is introduced into the heated bismuth compound, and the bismuth compound entrained in the carrier gas is introduced into a reaction chamber in which the substrate is placed; and a method in which the bismuth compound is sent to a vaporizer directly or as its solution dissolved in an organic solvent, gasified within the vaporizer, and then introduced into a reaction chamber in which the substrate is placed.

Examples of the organic solvent capable of dissolving the bismuth compound therein include alcohols (for example, methanol, ethanol, and isopropanol), esters (for example, ethyl acetate, butyl acetate, and isoamyl acetate), glycol ethers (for example, ethylene glycol monomethyl ether, ethylene glycol monoethyl ether, and ethylene glycol monobutyl ether), ethers (for example, glyme, diglyme, triglyme, and tetrahydrofuran), ketones (for example, methyl butyl ketone, methyl isobutyl ketone, ethyl butyl ketone, dipropyl ketone, diisobutyl ketone, methyl amyl ketone, and cyclohexanone), and hydrocarbons (for example, hexane, cyclohexane, methylcyclohexane, ethylcyclohexane, heptane, octane, toluene, and xylene). However, it should not be construed that the present invention is limited thereto.

With respect to the bismuth-containing film, for example, in the case where the bismuth compound of the present invention is used singly, metallic bismuth films or bismuth oxide films are obtained; and in the case where the bismuth compound is used in combination with other metal compound, bismuth-containing composite films are obtained. For example, when the bismuth compound is used in combination with a Ti compound, a BIT film is obtained; when the bismuth compound is used in combination with a Ti compound and an La compound, a BLT film is obtained; when the bismuth compound is used in combination with a Ti compound and an Nd compound, a BNT film is obtained; and when the bismuth compound is used in combination with an Sr compound and a Ta compound, an SBT film is obtained. However, it should not be construed that the present invention is limited thereto. Examples of the Ti compound, La compound, Nd compound, Sr compound and Ta compound include $Ti(O\text{-}iso\text{-}C_3H_7)_4$, $Ti(O\text{-}iso\text{-}C_3H_7)_2(DPM)_2$, $La(DPM)_3$, $Nd(DPM)_3$, $Sr[Ta(OEt)_6]_2$, $Sr[Ta(OEt)_5(OC_2H_4OCH_3)]_2$, $Sr(DPM)_2$, $Ta(O\text{-}Et)_5$, and $Ta(O\text{-}iso\text{-}C_3H_7)_5$. However it should not be construed that the present invention is limited thereto. Incidentally, the term "DPM" means dipivaloylmethanato. Also, in combining the bismuth compound with other metal compound, the respective compounds may be separately supplied, or may be mixed and then supplied. Also, with respect to the CVD process to be employed in the production of bismuth-containing films of the present invention, generally employed CVD processes such as thermal CVD, plasma CVD, and photo-CVD can be employed without particular limitations.

The third invention of this application will be described.

In the foregoing formulae 9 to 11, $R^{12}$ and $R^{13}$ each represents a lower alkyl group, a lower alkoxy group, a lower acyl group, a lower alkoxycarbonyl group, a lower halogenated alkyl group, or a halogen; m represents the number of the substituent $R^{12}$ in the range of 0–5; $n^3$ represents the number of the substituent $R^{13}$ in the range of 0–4; and $R^{14}$ to $R^{18}$ each represents hydrogen, a lower alkyl group, or a lower halogenated alkyl group.

The case where m is 4 or less, and/or $n^3$ is 3 or less means that hydrogen is bound to the aromatic ring. For example, the case where m is 0 means that two phenyl groups are bound to bismuth; and the case where m is 1, and $R^{12}$ represents a methyl group, two tolyl groups are bound to bismuth.

Examples of the lower alkyl group represented by $R^{12}$ and $R^{13}$ include a methyl group, an ethyl group, a n-propyl group, an isopropyl group, a n-butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclopropyl group, a cyclobutyl group, a cyclopentyl group, a cyclohexyl group, a cyclopropylmethyl group, a cyclopropylethyl group, and a cyclobutylmethyl group.

Examples of the lower alkoxy group represented by $R^{12}$ and $R^{13}$ include a methoxy group, an ethoxy group, a propoxy group, an isopropoxy group, a butoxy group, an isobutoxy group, a sec-butoxy group, a tert-butoxy group, a pentyloxy group, a 1-methylbutyloxy group, a 2-methylbutyloxy group, a 3-methylbutyloxy group, a 1,2-dimethylpropyloxy group, a hexyloxy group, a 1-methylpentyloxy group, a 1-ethylpropyloxy group, a 2-methylpentyloxy group, a 3-methylpentyloxy group, a 4-methylpentyloxy group, a 1,2-dimethylbutyloxy group, a 1,3-dimethylbutyloxy group, a 2,3-dimethylbutyloxy group, a 1,1-dimethylbutyloxy group, a 2,2-dimethylbutyloxy group, and a 3,3-dimethylbutyloxy group.

Examples of the lower acyl group represented by $R^{12}$ and $R^{13}$ include a formyl group, an acetyl group, a propionyl group, a butyryl group, an isobutyryl group, a valeryl group, a 1-methylpropylcarbonyl group, an isovaleryl group, a pentylcarbonyl group, a 1-methylbutylcarbonyl group, a 2-methylbutylcarbonyl group, a 3-methylbutylcarbonyl group, a 1-ethylpropylcarbonyl group, and a 2-ethylpropylcarbonyl group; examples of the lower alkoxycarbonyl group represented by $R^{12}$ and $R^{13}$ include a methoxycarbonyl group, an ethoxycarbonyl group, a propoxycarbonyl group, an isopropoxycarbonyl group, a cyclopropoxycarbonyl group, a butoxycarbonyl group, an isobutoxycarbonyl group, a sec-butoxycarbonyl group, and a tert-butoxycarbonyl group; examples of the lower halogenated alkyl group represented by $R^{12}$ and $R^{13}$ include a fluoromethyl group, a difluoromethyl group, and a trifluoromethyl group; and examples of the halogen represented by R$^{12}$ and R$^{13}$ include fluorine.

As R$^{14}$ to R$^{18}$, there are enumerated hydrogen; a lower alkyl group (for example, a methyl group, an ethyl group, a n-propyl group, an isopropyl group, a n-butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclopropyl group, a cyclobutyl group, a cyclopentyl group, a cyclohexyl group, a cyclopropylmethyl group, a cyclopropylethyl group, and a cyclobutylmethyl group); and a lower halogenated alkyl group (for example, a fluoromethyl group, a difluoromethyl group, and a trifluoromethyl group).

Although the bismuth compound of the present invention comprising a combination of R$^{12}$ to R$^{18}$ is not particularly limited, specific examples thereof include
di(4-propylphenyl)(2-(N,N-dimethylaminomethyl)-4-propylphenyl)bismuth,
di(4-acetylphenyl)(2-(N,N-dimethylaminomethyl)-4-propylphenyl)bismuth,
di(4-propylphenyl)(2-methoxymethyl-4-propylphenyl) bismuth, and
di(4-acetylphenyl)(2-methoxymethyl-4-propylphenyl) bismuth.

It is preferable from the standpoint of lowering the vaporization temperature of the bismuth compound that R$^{12}$ and R$^{13}$ each represents an alkyl group having 1–2 carbon atoms, R$^{14}$ and R$^{15}$ each represents hydrogen or an alkyl group having 1–2 carbon atoms, and R$^{16}$ to R$^{18}$ each represents an alkyl group having 1–2 carbon atoms. It is further preferable that R$^{12}$ and R$^{13}$ each represents an alkyl group having 1–2 carbon atoms, R$^{14}$ and R$^{15}$ each represents hydrogen or an alkyl group having 1–2 carbon atoms, R$^{16}$ to R$^{18}$ each represents an alkyl group having 1–2 carbon atoms, and m and n$^{3}$ are each 0–2.

Examples of such bismuth compounds include
di(2-tolyl)(2-(N,N-dimethylaminomethyl)phenyl)bismuth,
di(3-tolyl)(2-(N,N-dimethylaminomethyl)phenyl)bismuth,
diphenyl(2-(N,N-dimethylaminomethyl)-4-methylphenyl) bismuth,
di(2-tolyl)(2-(N,N-dimethylaminomethyl)-4-methylphenyl) bismuth,
di(3-tolyl)(2-(N,N-dimethylaminomethyl)-4-methylphenyl) bismuth,
di(4-tolyl)(2-(N,N-dimethylaminomethyl)-4-methylphenyl) bismuth,
di(2-ethylphenyl)(2-(N,N-dimethylaminomethyl)-4-methylphenyl)bismuth,
di(3-ethylphenyl)(2-(N,N-dimethylaminomethyl)-4-methylphenyl)bismuth,
di(4-ethylphenyl)(2-(N,N-dimethylaminomethyl)-4-methylphenyl)bismuth, and
diphenyl(2-(N,N-diethylaminomethyl)phenyl)bismuth.

There are further enumerated
di(2-tolyl)(2-(N,N-diethylaminomethyl)phenyl)bismuth,
di(3-tolyl)(2-(N,N-diethylaminomethyl)phenyl)bismuth,
di(4-tolyl)(2-(N,N-diethylaminomethyl)phenyl)bismuth,
diphenyl(2-(N,N-diethylaminomethyl)-4-methylphenyl) bismuth,
di(2-tolyl)(2-(N,N-diethylaminomethyl)-4-methylphenyl) bismuth,
di(3-tolyl)(2-(N,N-diethylaminomethyl)-4-methylphenyl) bismuth,
di(4-tolyl)(2-(N,N-diethylaminomethyl)-4-methylphenyl) bismuth,
di(2-ethylphenyl)(2-(N,N-diethylaminomethyl)-4-methylphenyl)bismuth,
di(3-ethylphenyl)(2-(N,N-diethylaminomethyl)-4-methylphenyl)bismuth,
di(4-ethylphenyl)(2-(N,N-diethylaminomethyl)-4-methylphenyl)bismuth, and
diphenyl(2-(N-ethyl-N-methylaminomethyl)phenyl) bismuth.

There are further enumerated
di(2-tolyl)(2-N-ethyl-N-methylaminomethyl)phenyl) bismuth,
di(3-tolyl)(2-N-ethyl-N-methylaminomethyl)phenyl) bismuth,
di(4-tolyl)(2-N-ethyl-N-methylaminomethyl)phenyl) bismuth,
diphenyl(2-(N-ethyl-N-methylaminomethyl)-4-methylphenyl)bismuth,
di(2-tolyl)(2-(N-ethyl-N-methylaminomethyl)-4-methylphenyl)bismuth,
di(3-tolyl)(2-(N-ethyl-N-methylaminomethyl)-4-methylphenyl)bismuth,
di(4-tolyl)(2-(N-ethyl-N-methylaminomethyl)-4-methylphenyl)bismuth,
di(2-ethylphenyl)(2-(N-ethyl-N-methylaminomethyl)-4-methylphenyl)bismuth,
di(3-ethylphenyl)(2-(N-ethyl-N-methylaminomethyl)-4-methylphenyl)bismuth, and
di(4-ethylphenyl)(2-(N-ethyl-N-methylaminomethyl)-4-methylphenyl)bismuth.

There are further enumerated diphenyl(2-(methoxymethyl)phenyl)bismuth,
di(2-tolyl)(2-(methoxymethyl)phenyl)bismuth,
di(3-tolyl)(2-(methoxymethyl)phenyl)bismuth,
di(4-tolyl)(2-(Methoxymethyl)phenyl)bismuth,
di(2-ethylphenyl)(2-(methoxymethyl)phenyl)bismuth,
di(3-ethylphenyl)(2-(methoxymethyl)phenyl)bismuth,
di(4-ethylphenyl)(2-(methoxymethyl)phenyl)bismuth,
diphenyl(2-(methoxymethyl)-4-methylphenyl)bismuth,
di(2-tolyl)(2-(methoxymethyl)-4-methylphenyl)bismuth,
di(3-tolyl)(2-(methoxymethyl)-4-methylphenyl)bismuth, and
di(4-tolyl)(2-(methoxymethyl)-4-methylphenyl)bismuth.

There are further enumerated
di(2-ethylphenyl)(2-(methoxymethyl)-4-methylphenyl) bismuth,
di(3-ethylphenyl)(2-(methoxymethyl)-4-methylphenyl) bismuth,
di(4-ethylphenyl)(2-(methoxymethyl)-4-methylphenyl) bismuth,
diphenyl(2-(ethoxymethyl)phenyl)bismuth,
di(2-tolyl)(2-(ethoxymethyl)phenyl)bismuth,
di(3-tolyl)(2-(ethoxymethyl)phenyl)bismuth,
di(4-tolyl)(2-(ethoxymethyl)phenyl)bismuth,
di(2-ethylphenyl)(2-(ethoxymethyl)phenyl)bismuth,
di(3-ethylphenyl)(2-(ethoxymethyl)phenyl)bismuth, and
di(4-ethylphenyl)(2-(ethoxymethyl)phenyl)bismuth.

There are further enumerated
diphenyl(2-(ethoxymethyl)-4-methylphenyl)bismuth,
di(2-tolyl)(2-(ethoxymethyl)-4-methylphenyl)bismuth,
di(3-tolyl)(2-(ethoxymethyl)-4-methylphenyl)bismuth,
di(4-tolyl)(2-(ethoxymethyl)-4-methylphenyl)bismuth, di(2-ethylphenyl)(2-(ethoxymethyl)-4-methylphenyl) bismuth,
di(3-ethylphenyl)(2-(ethoxymethyl)-4-methylphenyl) bismuth, and
di(4-ethylphenyl)(2-(ethoxymethyl)-4-methylphenyl) bismuth.

Of these, di(3-tolyl)(2-(N,N-dimethylaminomethyl)phenyl)bismuth and
diphenyl(2-(methoxymethyl)phenyl)bismuth are more preferable.

The bismuth compound represented by the formula 9 according to the present invention can be produced by mixing and reacting a diaryl monohalogeated bismuth represented by the formula 12 with an arylating reagent represented by the formula 13 in a solvent. At this time, when the amount of the arylating reagent is in excess, a triaryl bismuth is likely formed, thereby reducing the yield. Therefore, it is preferred to use the arylating reagent in an amount of 1 time by mole against the diaryl monohalogenated bismuth. In mixing these compounds, a solution or suspension of the arylating reagent may be dropped in a solution or suspension of the diaryl monohalogenated bismuth, or a solution or suspension of the diaryl monohalogenated bismuth may be dropped in a solution or suspension of the arylating reagent. In this regard, when dropping is carried out at a low temperature (from about −80° C. to −40° C.), it is possible to obtain the desired bismuth compound of the present invention in a high yield, and therefore, such is preferable.

The diaryl monohalogenated bismuth to be used can be synthesized by, for example, mixing a triaryl bismuth and a trihalogenated bismuth in a proportion of 2/1 (by mole) in a solvent (*J. Chem. Soc.*, 107, 16 (1915)). In the diaryl monohalogenated bismuth represented by the formula 12, $Z^3$ represents a halogen, examples of which include chlorine, bromine, and iodine. Also, in the arylating reagent represented by the formula 13, $Q^3$ represents an alkali metal such as lithium, sodium, and potassium, or MgBr, MgCl, or MgI.

As the solvent, those which are liquid at −80° C. are preferable but are not particularly limited. Preferred examples thereof include diethyl ether, THF, toluene, and hexane. The solvent may be used alone or as a mixture. The solvent to be used in the solution or suspension of the diaryl monohalogenated bismuth and the solvent used in the solution or suspension of the arylating reagent are not necessarily required to be identical with each other but may be different from each other. With respect to the reaction temperature, the reaction rate is slow at low temperatures, and a trialkyl bismuth may possibly be formed at high temperatures. Accordingly, it is preferable that dropping and mixing are carried out at a low temperature (from −80 to −40° C.) and that the reaction temperature is gradually raised to −10 to 30° C. After the reaction, the reaction mixture is quenched with water or the like, and the desired bismuth compound of the present invention can be recovered from an oily layer. Since the oily layer contains diaryl compound and the like formed by the reaction in addition to the desired bismuth compound, the oily layer is purified by chromatography, distillation, sublimation, recrystallization, or the like, thereby obtaining the desired bismuth compound of the present invention.

Since the bismuth compound according to the first invention or second invention of this application can be vaporized to an extent of 100%, and the decomposition temperature is sufficiently higher than the vaporization temperature, it is suitable as a bismuth precursor in the CVD process. In particular, in the film formation by the CVD process, the bismuth compound of the present invention gives rise to the following advantages as compared with known triphenylbismuth.

(1) The vaporization characteristic is excellent.
(2) Since a difference between the vaporization temperature and the decomposition temperature is large, it is possible to stably supply a precursor in the case where the bismuth compound of the present invention is used in the CVD process.
(3) The bismuth compound of the present invention is liquid at room temperature so that it is possible to easily supply the same.

Since the bismuth compound according to the third invention of this application can be vaporized to an extent of 100%, and the decomposition temperature is sufficiently higher than the vaporization temperature, it can be sufficiently expected to employ the bismuth compound of the present invention in the CVD process. The bismuth compound of the present invention is superior in thermal stability to conventionally used triphenylbismuth in the film formation by the CVD process, and therefore, it is possible to stably supply the same.

The present invention is described in more detail by reference to the following Examples, but it should be understood that the present invention is not construed as being limited thereto.

EXAMPLE 1

A 50 ml three-necked flask was charged with 3.30 g (8.0 mmoles) of dichloro(2-(N,N-dimethylaminomethyl)phenyl)bismuth, equipped with a dropping funnel and a thermometer, and then purged with argon. 40 ml of diethyl ether was added and stirred to disperse the dichloro(2-(N,N-dimethylaminomethyl)phenyl)bismuth. 25 ml (15.0 mmoles) of a solution of 0.6 moles/liter of methyl magnesium bromide in diethyl ether was dropped over 30 minutes from the dropping funnel while keeping the temperature at −80° C. or lower. After completion of dropping, the mixture was stirred at −80° C. for 2 hours and then stirred at room temperature for 22 hours. After the reaction, the reaction mixture was quenched with a saturated ammonium chloride aqueous solution, and then separated into an aqueous layer and an organic layer. The aqueous layer was extracted thrice with 10 ml of diethyl ether. The organic layer and the extracts were gathered, and the mixture was rinsed thrice with 20 ml of a saturated salt aqueous solution. The resulting mixture was dried over anhydrous magnesium sulfate and then filtered. The solvent was removed from the filtrate, to obtain 2.53 g of a cloudy oil. 0.96 g of the cloudy oil was distilled under reduced pressure to obtain 0.54 g (yield: 48%) of dimethyl(2-(N,N-dimethylaminomethyl)phenyl)bismuth as a colorless transparent liquid.

$^1$H-NMR (CDCl$_3$) δ7.95 (d, 1H, J=7.0 Hz), 7.22 (m, 2H), 7.15 (d, 1H, J=7.0 Hz), 3.45 (s, 2H), 2.17 (s, 6H), 1.06 (s, 6H).

$^{13}$C-NMR (CDCl$_3$) δ177.53 (C), 144.53 (C), 137.07 (CH), 128.60 (CH), 128.57 (CH), 126.90 (CH), 67.66 (CH$_2$), 44.80 (CH$_3$), 3.08 (CH$_3$).

MS: m/z=374 (M$^+$+H), 358 (M-CH$_3$), 343 (M-2CH$_3$), 239 (M-C$_9$H$_{12}$N), 224 (M-C$_9$H$_{12}$N—CH$_3$).

Elemental analysis: C (35.6%), H (5.0%), N (3.7%), Bi (53.5%); Calculated: C (35.4%), H (4.9%), N (3.8%), Bi (56.0%).

EXAMPLE 2

A 50 ml three-necked flask was charged with 0.98 g (2.4 mmoles) of dichloro(2-(methoxymethyl)phenyl)bismuth, equipped with a dropping funnel and a thermometer, and then purged with argon. 10 ml of diethyl ether was added and stirred to disperse the dichloro(2-(methoxymethyl) phenyl)bismuth. 6.5 ml (4.9 mmoles) of a solution of 0.75 moles/liter of methyl magnesium bromide in diethyl ether was dropped over 10 minutes from the dropping funnel while keeping the temperature at −80° C. or lower. After completion of dropping, the mixture was stirred at −80° C. for 2 hours and then stirred at room temperature for 20 hours. After the reaction, the reaction mixture was quenched with a saturated ammonium chloride aqueous solution, and then separated into an aqueous layer and an organic layer. The aqueous layer was extracted twice with 10 ml of diethyl ether. The organic layer and the extracts were gathered, and the mixture was rinsed thrice with 10 ml of a saturated salt aqueous solution. The resulting mixture was dried over anhydrous magnesium sulfate and then filtered. The solvent was removed from the filtrate, to obtain 0.54 g of a cloudy oil. The resulting cloudy oil was distilled under reduced pressure to obtain 0.18 g (yield: 20%) of dimethyl(2-(methoxymethyl)phenyl)bismuth as a colorless transparent liquid.

$^1$H-NMR (CDCl$_3$) δ7.95 (d, 1H, J=7.0 Hz), 7.28 (m, 3H), 4.51 (s, 2H), 3.35 (s, 3H), 1.21 (s, 6H).

$^{13}$C-NMR (CDCl$_3$) δ143.29 (C), 141.79 (C), 137.36 (CH), 129.72 (CH), 128.57 (CH), 127.52 (CH), 78.39 (CH$_2$), 57.92 (CH$_3$), 2.79 (CH$_3$).

EXAMPLE 3

A 50 ml three-necked flask was charged with 0.200 g of di(3-tolyl)monochlorobismuth, equipped with a dropping funnel and a thermometer, and then purged with argon. 2 ml of diethyl ether was added and stirred to disperse the di(3-tolyl)monochlorobismuth. A suspension of 0.068 g of 2-(N,N-dimethylaminomethyl)phenyllithium salt synthesized from N,N-dimethylbenzylamine and n-butyllithium in 2 ml of diethyl ether was dropped over 30 minutes from the dropping funnel while keeping the temperature at −50° C. or lower. After completion of dropping, the mixture was stirred for 3 hours while gradually raising the temperature to 10° C. After the reaction, the reaction mixture was quenched with a saturated ammonium chloride aqueous solution, and then separated into an aqueous layer and an organic layer. The aqueous layer was extracted thrice with 10 ml of diethyl ether. The organic layer and the extracts were gathered, and the mixture was rinsed twice with 20 ml of a saturated salt aqueous solution. The resulting mixture was dried over anhydrous magnesium sulfate and then filtered. The solvent was removed from the filtrate, to obtain 0.169 g of a white powder. The resulting white powder was recrystallized from diethyl ether/hexane, to obtain 0.088 g (yield: 36%) of di-(3-tolyl)(2-(N,N-dimethylaminomethyl)phenyl)bismuth as a white crystal.

$^1$H-NMR (CDCl$_3$) δ7.81 (d, 1H, J=7.5 Hz), 7.59 (s, 2H), 7.53 (d, 2H, J=7.5 Hz), 7.24 (m, 4H), 7.08 (d, 2H, J=8.0 Hz), 3.41 (s, 2H), 2.28 (s, 6H), 1.98 (s, 6H).

Figure 13:
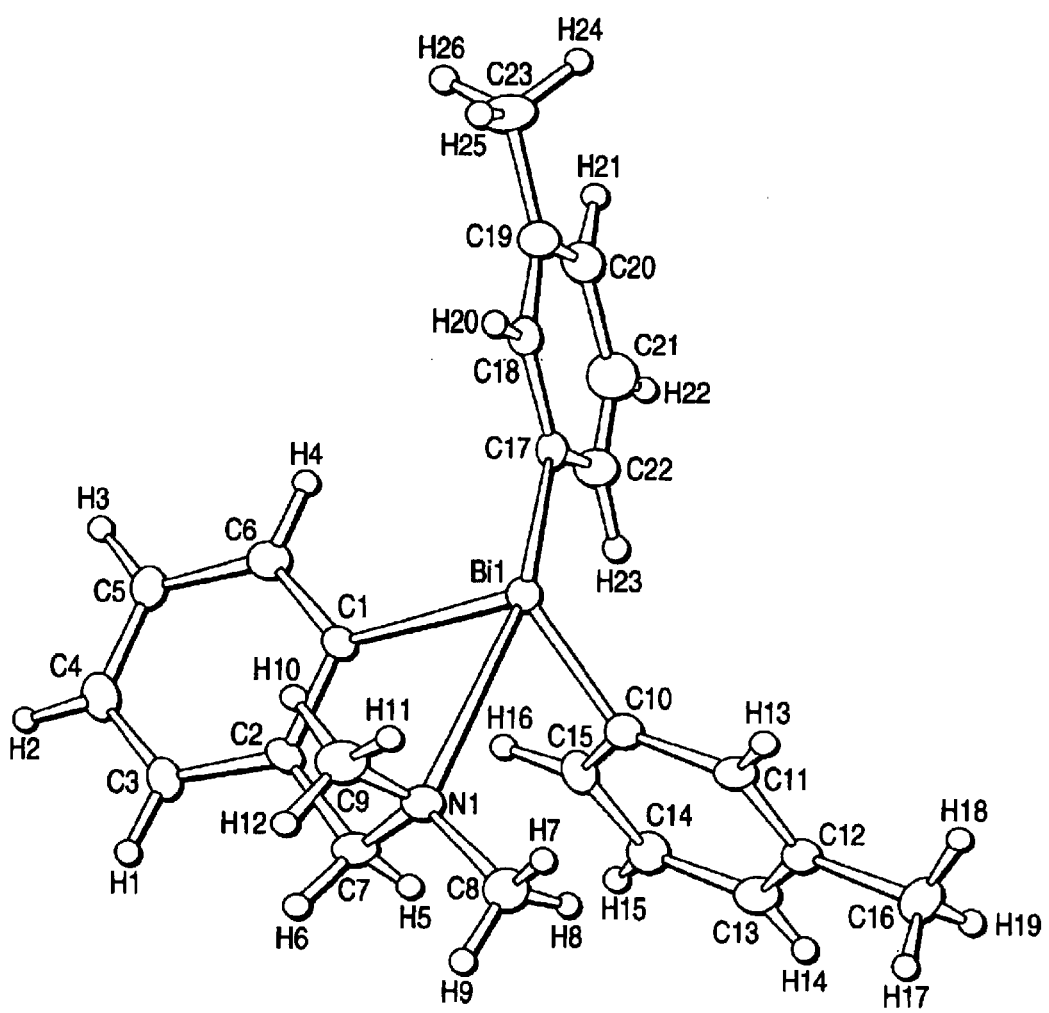
FIG. 13 is a view showing an X-ray structure of a single crystal of di(3-tolyl)(2-(N,N-dimethylaminomethyl)phenyl)bismuth.

An X-ray structure of the resulting single crystal of di(3-tolyl)(2-(N,N-dimethylaminomethyl)phenyl)bismuth is shown in FIG. 13. As is clear from this drawing, it could be confirmed that the desired compound was synthesized.

EXAMPLE 4

A 100 ml three-necked flask equipped with a dropping funnel and a thermometer was purged with argon and then charged with 0.260 g (1.29 mmoles) of 2-bromobenzyl methyl ether and 4 ml of THF. A solution of 1.25 mmoles of n-butyllithium in hexane was dropped from the dropping funnel while keeping the temperature at −80° C., and the mixture was stirred for one hour. Subsequently, a solution of 0.502 g (1.26 mmoles) of diphenylmonochlorobismuth in 8 ml of THF was dropped from the dropping funnel while keeping the temperature at −80° C. After completion of dropping, the mixture was stirred at −80° C. for 2 hours and further stirred at room temperature for 40 hours. After the reaction, the reaction mixture was quenched with a saturated ammonium chloride aqueous solution, and then separated into an aqueous layer and an organic layer. The aqueous layer was extracted thrice with 10 ml of diethyl ether. The organic layer and the extracts were gathered, and the mixture was rinsed twice with 20 ml of a saturated salt aqueous solution. The resulting mixture was dried over anhydrous magnesium sulfate and then filtered. The solvent was removed from the filtrate, to obtain 0.552 g of a white powder. 0.397 g of the resulting white powder was purified by column chromatography using alumina as a filler and hexane/ethyl acetate (50/1) as a solvent, and the solvent was then removed to obtain 0.246 g of diphenyl(2-(methoxymethyl)phenyl)bismuth as a white powder. The yield of the diphenyl(2-(methoxymethyl)phenyl)bismuth was calculated to be 56%.

$^1$H-NMR (CDCl$_3$) δ7.80 (d, 1H, J=7.5 Hz), 7.73 (d, 4H, J=8.0 Hz), 7.37 (m, 5H), 7.31 (m, 3H), 7.22 (t, 1H, J=7.5 Hz), 4.47 (s, 2H), 3.17 (s, 3H).

EXAMPLE 5

22.1 mg (0.059 mmoles) of dimethyl(2-(N,N-dimethylaminomethyl)phenyl)bismuth obtained in Example 1 was charged in an aluminum pan. This sample was analyzed for a change of the weight upon heating by an apparatus for thermogravity (TG) at a programming rate of 10° C. per minute using 6.7 mg of aluminum oxide as a reference. The results are shown in FIG. 1. As is clear from this drawing, in dimethyl(2-(N,N-dimethylaminomethyl) phenyl)bismuth of the present invention, a weight reduction was observed from about 130° C., and it was confirmed that this compound was vaporized to an extent of substantially 100%.

EXAMPLE 6

Figure 2:
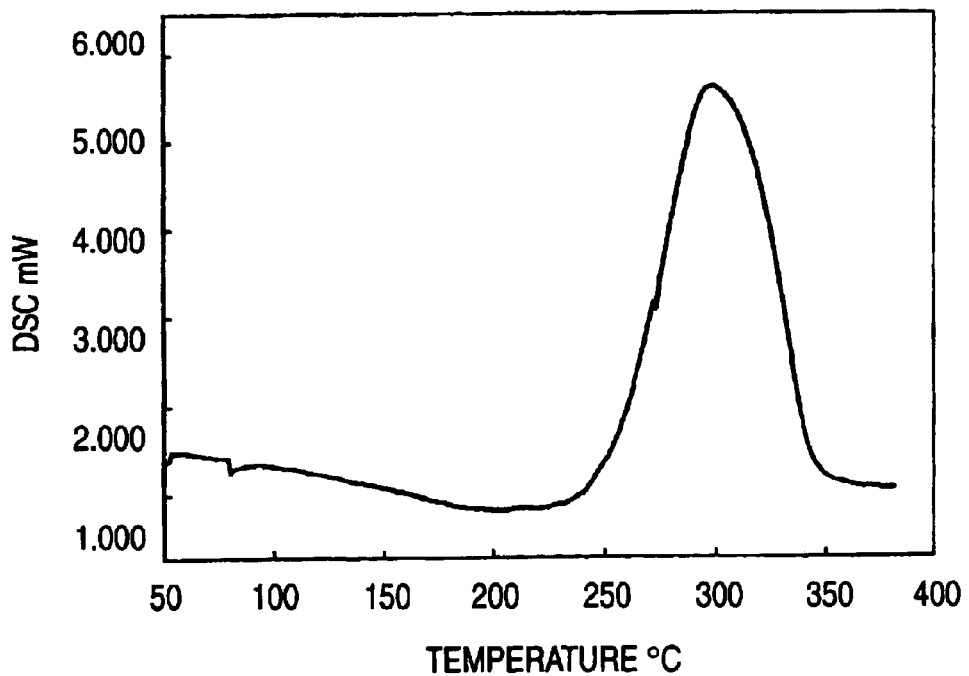
FIG. 2 is a graph showing a DSC curve of Example 6.

3.5 mg of dimethyl(2-(N,N-dimethylaminomethyl) phenyl)bismuth obtained in Example 1 was taken into a stainless steel pan, which was then sealed by a stainless steel lid. This sample was analyzed for a change of the quantity of heat upon heating by a differential scanning calorimeter (DSC) at a programming rate of 10° C. per minute using 2.0 mg of aluminum oxide as a reference. The results are shown in FIG. 2. As is clear from this drawing, exothermic reaction was observed from about 230° C., and decomposition of dimethyl(2-(N,N-dimethylaminomethyl)phenyl)bismuth was confirmed. It is noted that the exothermic reaction proceeds gently and that gentle decomposition advances.

EXAMPLE 7

Figure 3:
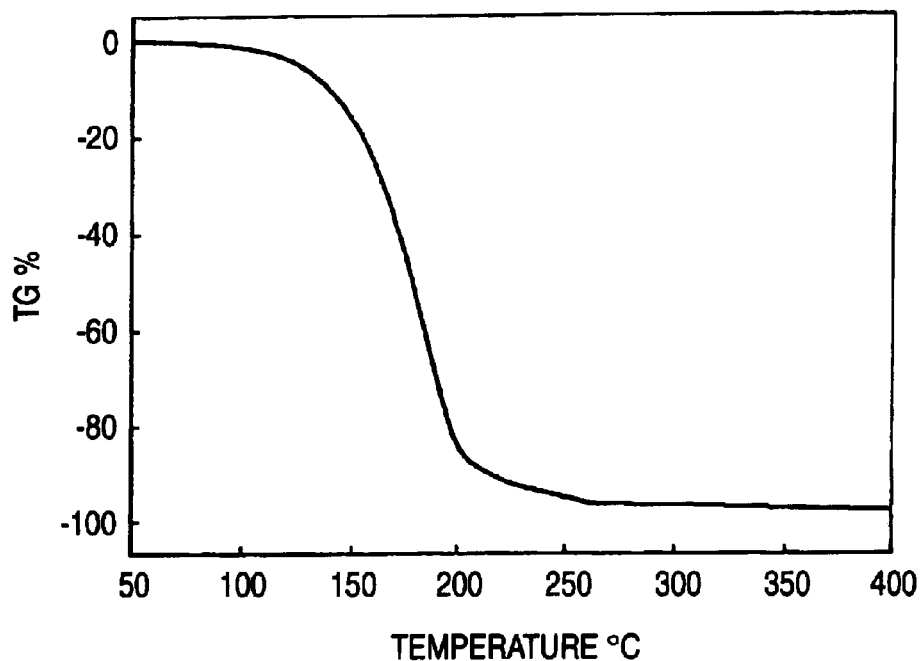
FIG. 3 is a graph showing a TG curve of Example 7.

10.4 mg (0.029 mmoles) of dimethyl(2-(methoxymethyl) phenyl)bismuth obtained in Example 2 was charged in an aluminum pan. This sample was analyzed for a change of the weight upon heating by an apparatus for thermogravity (TG) at a programming rate of 10° C. per minute using 14.9 mg of aluminum oxide as a reference. The results are shown in FIG. 3. As is clear from this drawing, in dimethyl(2-(methoxymethyl)phenyl)bismuth of the present invention, a weight reduction was observed from about 130° C., and it was confirmed that this compound was vaporized to an extent of substantially 100%.

EXAMPLE 8

Figure 4:
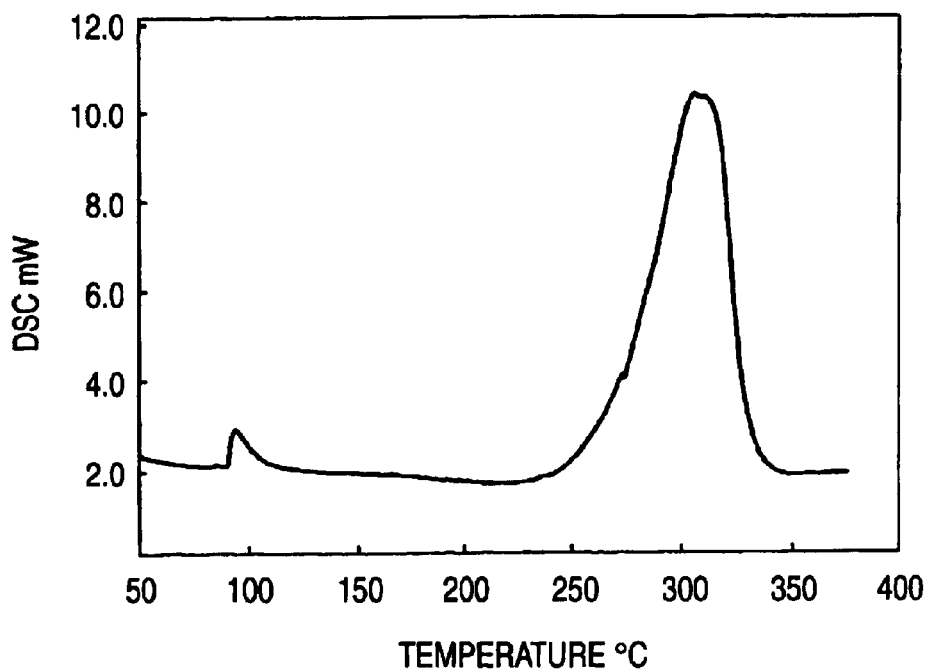
FIG. 4 is a graph showing a DSC curve of Example 8.

4.2 mg of dimethyl(2-(methoxymethyl)phenyl)bismuth obtained in Example 2 was taken into a stainless steel pan, which was then sealed by a stainless steel lid. This sample was analyzed for a change of the quantity of heat upon heating by a differential scanning calorimeter (DSC) at a programming rate of 10° C. per minute using 2.0 mg of aluminum oxide as a reference. The results are shown in FIG. 4. As is clear from this drawing, exothermic reaction was observed from about 230° C., and decomposition of dimethyl(2-(methoxymethyl)phenyl)bismuth was confirmed. It is noted that the exothermic reaction proceeds gently and that gentle decomposition advances.

EXAMPLE 9

Figure 5:
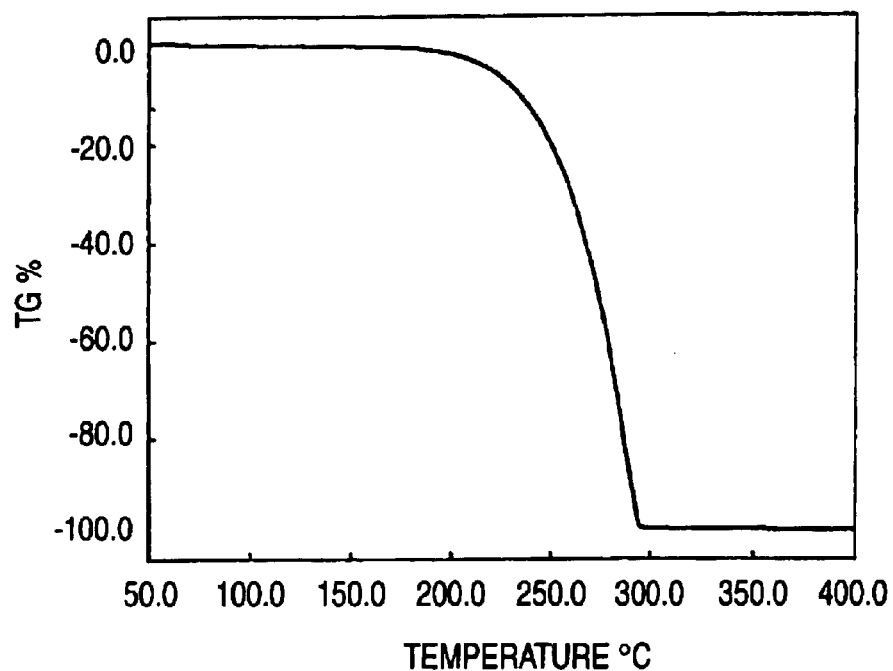
FIG. 5 is a graph showing a TG curve of Example 9.

5.9 mg (0.011 mmoles) of di(3-tolyl)(2-(N,N-dimethylaminomethyl)phenyl)bismuth obtained in Example 3 was charged in an aluminum pan. This sample was analyzed for a change of the weight upon heating by an apparatus for thermogravity (TG) at a programming rate of 10° C. per minute using 8.9 mg of aluminum oxide as a reference. A weight reduction was observed from about 230° C., and it was confirmed that this compound was vaporized to an extent of substantially 100%. The results are shown in FIG. 5.

EXAMPLE 10

Figure 6:
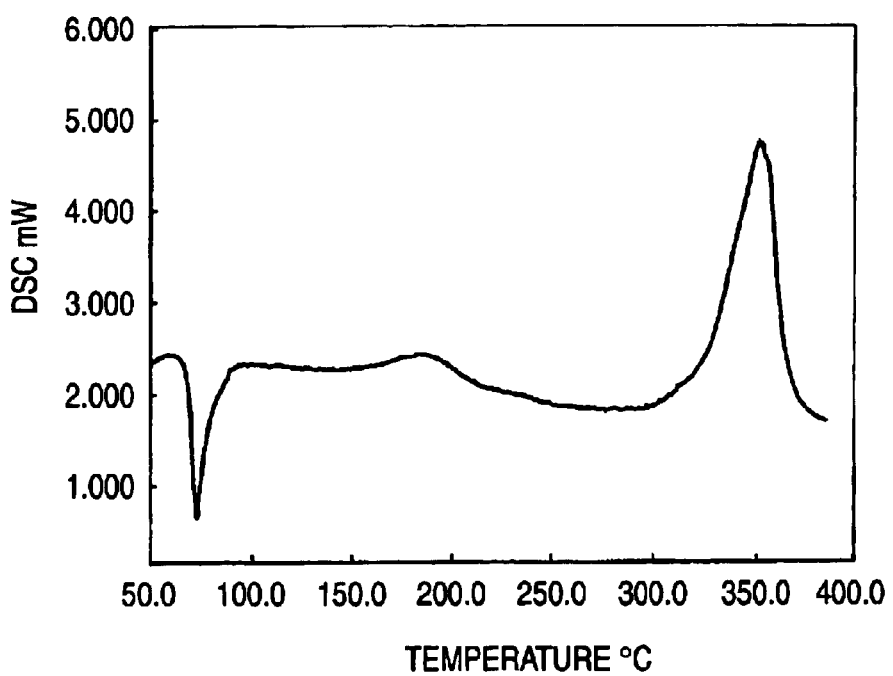
FIG. 6 is a graph showing a DSC curve of Example 10.

1.9 mg of di(3-tolyl)(2-(N,N-dimethylaminomethyl) phenyl)bismuth obtained in Example 3 was taken into a stainless steel pan, which was then sealed by a stainless steel lid. This sample was analyzed for a change of the quantity of heat upon heating by a differential scanning calorimeter (DSC) at a programming rate of 10° C. per minute using 2.0 mg of aluminum oxide as a reference. Exothermic reaction was observed from about 290° C., and decomposition of di(3-tolyl)(2-(N,N-dimethylaminomethyl)phenyl)bismuth was confirmed. The results are shown in FIG. 6.

EXAMPLE 11

Figure 7:
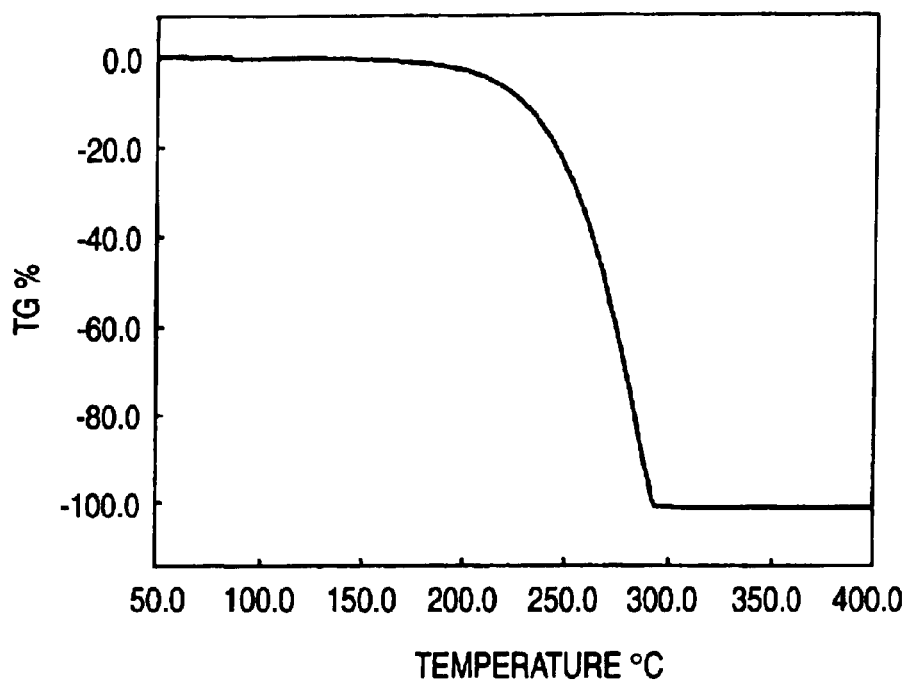
FIG. 7 is a graph showing a TG curve of Example 11.

5.5 mg (0.011 mmoles) of diphenyl(2-(methoxymethyl) phenyl)bismuth obtained in Example 4 was charged in an aluminum pan. This sample was analyzed for a change of the weight upon heating by an apparatus for thermogravity (TG) at a programming rate of 10° C. per minute using 7.7 mg of aluminum oxide as a reference. A weight reduction was observed from about 225° C., and it was confirmed that this compound was vaporized to an extent of substantially 100%. The results are shown in FIG. 7.

EXAMPLE 12

Figure 8:
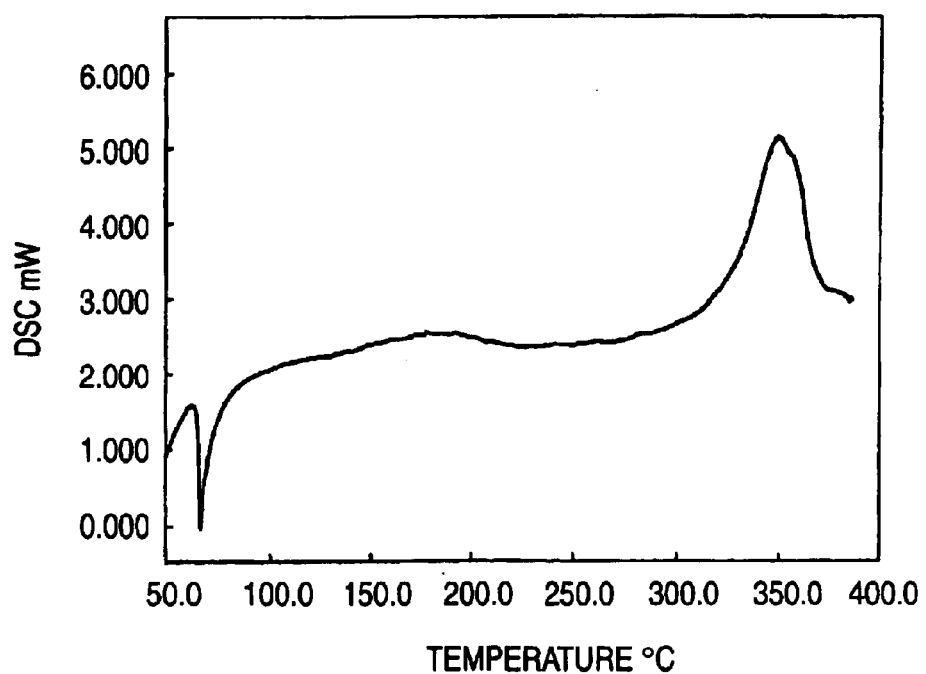
FIG. 8 is a graph showing a DSC curve of Example 12.

1.8 mg of diphenyl(2-(methoxymethyl)phenyl)bismuth obtained in Example 4 was taken into a stainless steel pan, which was then sealed by a stainless steel lid. This sample was analyzed for a change of the quantity of heat upon heating by a differential scanning calorimeter (DSC) at a programming rate of 10° C. per minute using 2.0 mg of aluminum oxide as a reference. Exothermic reaction was observed from about 290° C., and decomposition of diphenyl(2-(methoxymethyl)phenyl)bismuth was confirmed. The results are shown in FIG. 8.

EXAMPLE 13

Figure 12:
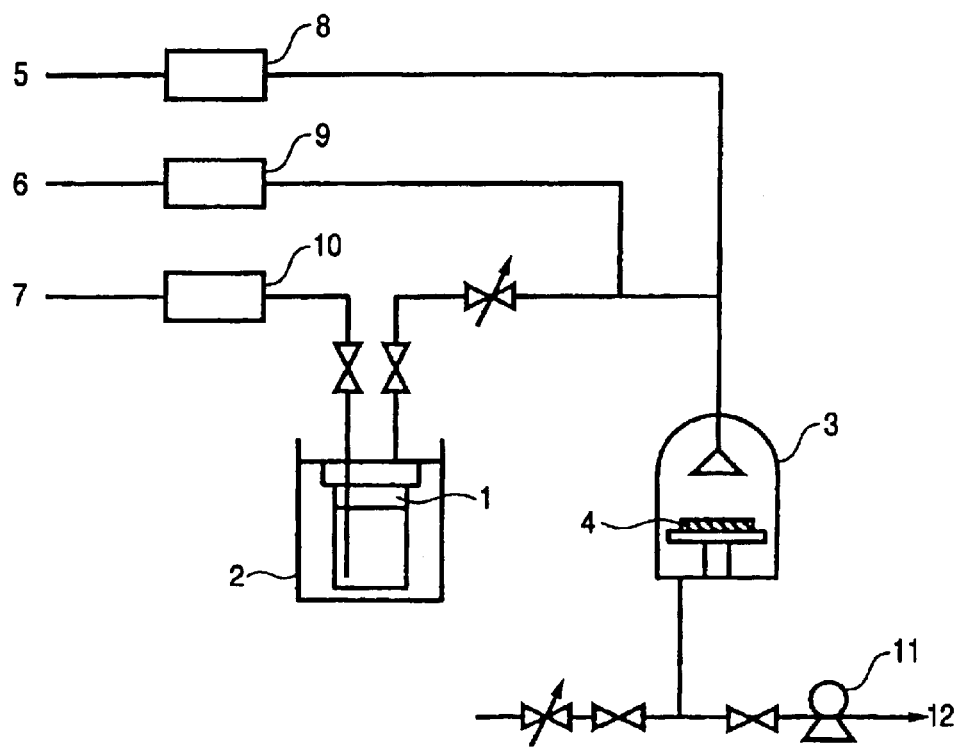
FIG. 12 is a view showing a CVD apparatus used in Examples 13 and 14.

Dimethyl(2-(N,N-dimethylaminomethyl)phenyl)bismuth obtained in Example 1 was used as a precursor and subjected to film formation on an $SiO_2$/Si substrate for one hour by the CVD process using an apparatus shown in FIG. 12 under the following conditions. Precursor temperature: 55° C., flow rate of carrier gas (Ar): 50 sccm, vessel pressure: 100 Torr, flow rate of diluent gas (Ar): 100 sccm, flow rate of reaction gas ($O_2$): 300 sccm, substrate temperature: 500° C., decomposition pressure: 10 Torr. The X-ray diffraction analysis revealed that the film was $Bi_2O_3$, and the SEM analysis revealed that the film thickness was 200 nm.

EXAMPLE 14

Dimethyl(2-(methoxymethyl)phenyl)bismuth obtained in Example 2 was used as a precursor and subjected to film formation on an $SiO_2$/Si substrate for one hour by the CVD process using an apparatus shown in FIG. 12 under the following conditions. Precursor temperature: 55° C., flow rate of carrier gas (Ar): 50 sccm, vessel pressure: 100 Torr, flow rate of diluent gas (Ar): 100 sccm, flow rate of reaction gas ($O_2$): 300 sccm, substrate temperature: 500° C., decomposition pressure: 10 Torr. The X-ray diffraction analysis revealed that the film was $Bi_2O_3$, and the SEM analysis revealed that the film thickness was 150 nm.

EXAMPLE 15

Figure 14:
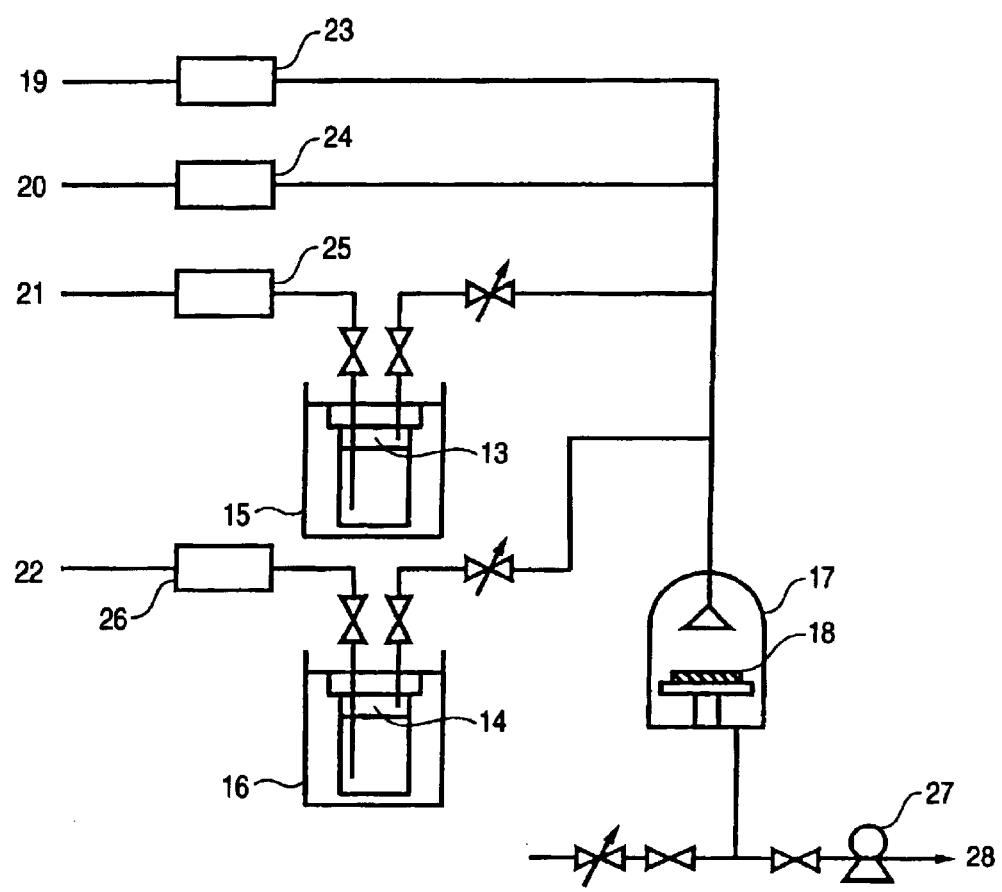
FIG. 14 is a view showing a CVD apparatus used in Example 15.

Dimethyl(2-(N,N-dimethylaminomethyl)phenyl)bismuth obtained in Example 1 and $Ti(O-iso-C_3H_7)_4$ were used as precursors and subjected to film formation on a $Pt/TiO_x/SiO_2$/Si substrate for one hour by the CVD process using an apparatus shown in FIG. 14 under the following conditions. Bismuth precursor temperature: 67° C., flow rate of carrier gas (Ar) for bismuth precursor: 20 sccm, vessel pressure for bismuth precursor: 300 Torr, titanium precursor temperature: 31° C., flow rate of carrier gas (Ar) for titanium precursor: 30 sccm, vessel pressure for titanium precursor: 300 Torr, flow rate of diluent gas (Ar): 150 sccm, flow rate of reaction gas ($O_2$): 200 sccm, substrate temperature: 500° C., decomposition pressure: 4 Torr. The X-ray diffraction analysis revealed that the film was BIT, and the SEM analysis revealed that the film thickness was 300 nm.

COMPARATIVE EXAMPLE 1

Figure 9:
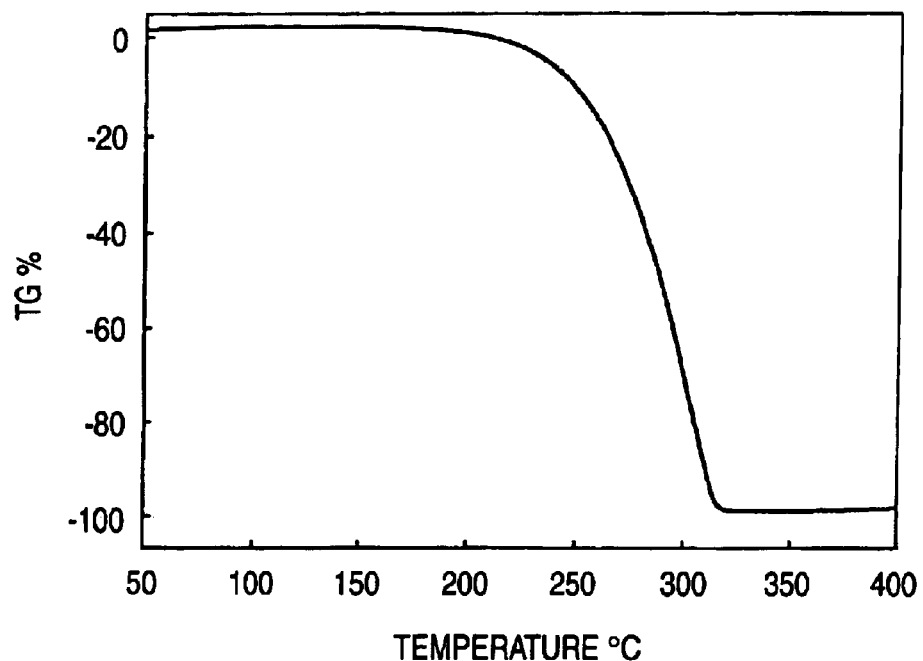
FIG. 9 is a graph showing a TG curve of Comparative Example 1.

25.7 mg (0.058 mmoles) of triphenylbismuth was analyzed for a change of the weight upon heating using 17.7 mg of aluminum oxide as a reference in the same manner as in Example 5. The results are shown in FIG. 9. As is clear from this drawing, a weight reduction was observed from about 230° C., and it is noted that the vaporization temperature of triphenylbismuth is about 100° C. higher than that of dimethyl(2-(N,N-dimethylaminomethyl)phenyl)bismuth.

COMPARATIVE EXAMPLE 2

Figure 10:
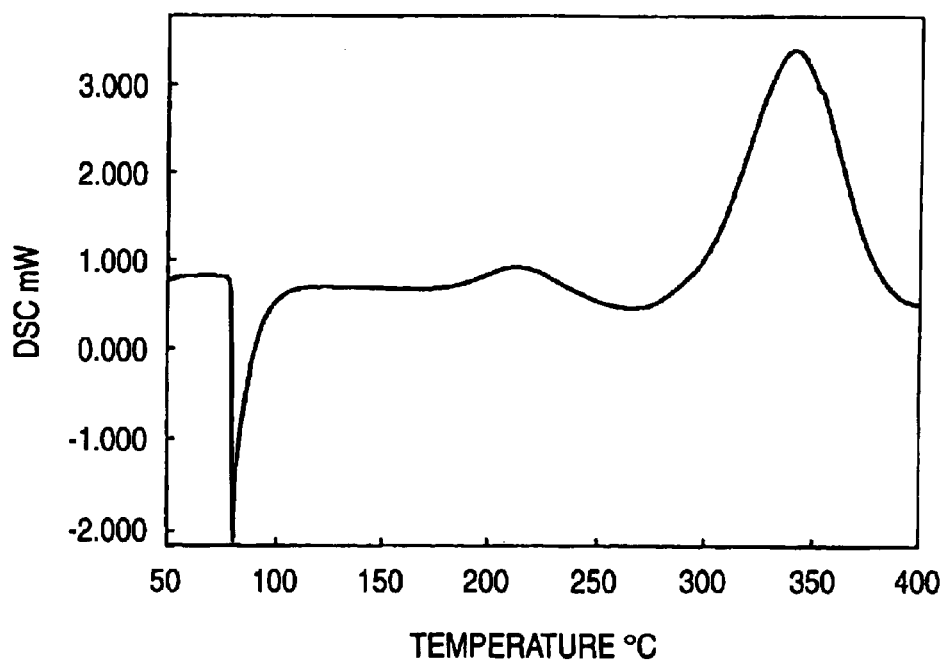
FIG. 10 is a graph showing a DSC curve of Comparative Example 2.

2.6 mg of triphenylbismuth was analyzed for a change of the quantity of heat upon heating using 7.2 mg of aluminum oxide as a reference in the same manner as in Example 6. The results are shown in FIG. 10. As is clear from this drawing, exothermic reaction was observed from about 270° C., and the thermal decomposition temperature of triphenylbismuth was about 40° C. higher than that of dimethyl(2-(N,N-di-methylaminomethyl)phenyl)bismuth and that of dimethyl(2-(methoxymethyl)phenyl)bismuth, about 25° C. lower than that of di(3-tolyl)(2-(N,N-dimethylaminomethyl) phenyl)bismuth and about 20° C. lower than that of diphenyl (2-(methoxymethyl)phenyl)bismuth, respectively.

COMPARATIVE EXAMPLE 3

Figure 11:
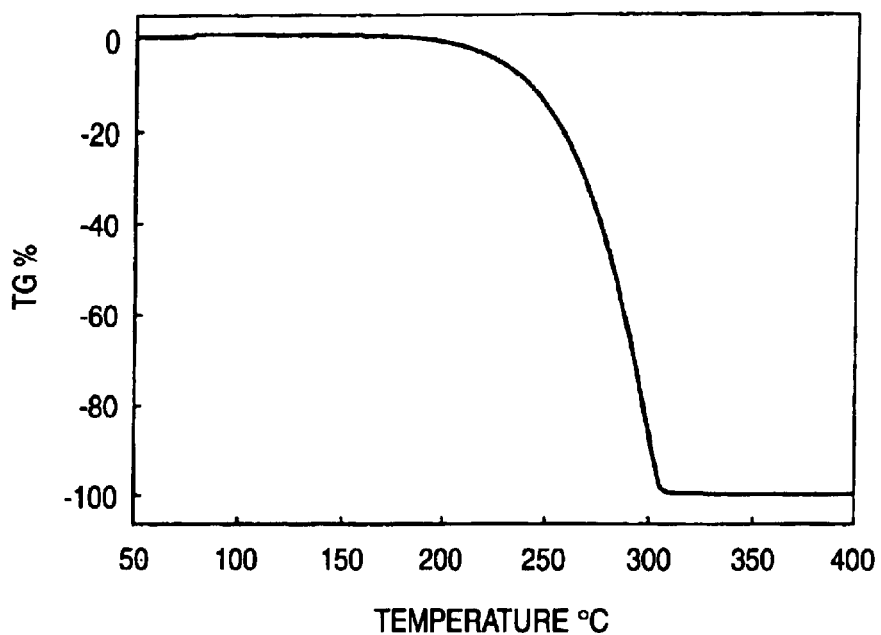
FIG. 11 is a graph showing a TG curve of Comparative Example 3.

13.0 mg (0.030 mmoles) of triphenylbismuth was analyzed for a change of the weight upon heating using 14.9 mg of aluminum oxide as a reference in the same manner as in Example 7. The results are shown in FIG. 11. As is clear from this drawing, a weight reduction was observed from about 230° C., and it is noted that the vaporization temperature of triphenylbismuth is about 100° C. higher than that of dimethyl(2-(methoxymethyl)phenyl)bismuth.

The following can be understood from the above Examples and Comparative Examples.

(1) With respect to the vaporization temperature, it is noted from the comparison between Example 5 and Comparative Example 1 that dimethyl(2-(N,N-dimethylaminomethyl)phenyl)bismuth according to the present invention has a vaporization temperature of about 100° C. lower than that of known triphenylbismuth and is excellent in vaporization characteristic.

(2) With respect to a difference between the vaporization temperature and the decomposition temperature, as described above in (1), dimethyl(2-(N,N-dimethylaminomethyl)phenyl)bismuth according to the present invention has a vaporization temperature of about 100° C. lower than that of known triphenylbismuth. On the other hand, it is noted from the comparison between Example 6 and Comparative Example 2 that dimethyl(2-(N,N-dimethylaminomethyl)phenyl)bismuth according to the present invention has a decomposition temperature of about 40° C. lower than that of known triphenylbismuth. When a difference between the vaporization temperature and the decomposition temperature with respect to the both compounds is calculated from the foregoing results, it is noted that in dimethyl(2-(N,N-dimethylaminomethyl) phenyl)bismuth according to the present invention, the difference between the vaporization temperature and the decomposition temperature is very large and is increased by about 60° C. as compared with known triphenylbismuth.

(3) With respect to the vaporization temperature, it is noted from the comparison between Example 7 and Comparative Example 3 that dimethyl(2-(methoxymethyl)phenyl) bismuth according to the present invention has a vaporization temperature of about 100° C. lower than that of known triphenylbismuth and is excellent in vaporization characteristic.

(4) With respect to a difference between the vaporization temperature and the decomposition temperature, as described above in (3), dimethyl(2-(methoxymethyl) phenyl)bismuth according to the present invention has a vaporization temperature of about 100° C. lower than that of known triphenylbismuth. On the other hand, it is noted from the comparison between Example 8 and Comparative Example 2 that dimethyl(2-(methoxymethyl)phenyl) bismuth according to the present invention has a decomposition temperature of about 40° C. lower than that of known triphenylbismuth. When a difference between the vaporization temperature and the decomposition temperature with respect to the both compounds is calculated from the foregoing results, it is noted that in dimethyl(2-(methoxymethyl)phenyl)bismuth according to the present invention, the difference between the vaporization temperature and the decomposition temperature is very large and is increased by about 60° C. as compared with known triphenylbismuth.

What is claimed is:

1. A bismuth compound represented by the following formula 1:

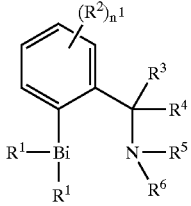

wherein $R^1$ represents a lower alkyl group; $R^2$ represents a lower alkyl group, a lower alkoxy group, a lower acyl group, a lower alkoxycarbonyl group, a lower halogenated alkyl group, or a halogen; $n^1$ represents the number of the substituent $R^2$ in the range of 0–4; and $R^3$ to $R^6$ each represents hydrogen, a lower alkyl group, or a lower halogenated alkyl group.

2. The bismuth compound as claimed in claim 1, wherein $R^1$ represents a methyl group; $R^2$ represents an alkyl group having 1–2 carbon atoms; $R^3$ and $R^4$ each represents hydrogen or an alkyl group having 1–2 carbon atoms; and $R^5$ and $R^6$ each represents an alkyl group having 1–2 carbon atoms.

3. The bismuth compound as claimed in claim 2, wherein $R^1$ represents a methyl group; $R^3$ and $R^4$ each represents hydrogen; $R^5$ and $R^6$ each represents a methyl group; and $n^1$ is 0.

4. A process of producing a bismuth compound as claimed in any one of claims 1 to 3, which comprises reacting a monoaryl dihalogenated bismuth represented by the following formula 2:

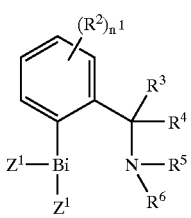

wherein $R^2$ represents a lower alkyl group, a lower alkoxy group, a lower acyl group, a lower alkoxycarbonyl group, a lower halogenated alkyl group, or a halogen; $n^1$ represents the number of the substituent $R^2$ in the range of 0–4; $R^3$ to $R^6$ each represents hydrogen, a lower alkyl group, or a lower halogenated alkyl group; and $Z^1$ represents a halogen, with an $R^1$-converting reagent, wherein $R^1$ represents a lower alkyl group.

5. A process of producing a bismuth compound as claimed in any one of claims 1 to 3, which comprises reacting a dialkyl monohalogenated bismuth represented by the following formula 3:

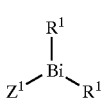

wherein $R^1$ represents a lower alkyl group; and $Z^1$ represents a halogen, with an arylating reagent represented by the following formula 4:

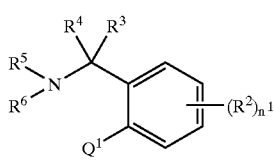

wherein $R^2$ represents a lower alkyl group, a lower alkoxy group, a lower acyl group, a lower alkoxycarbonyl group, a lower halogenated alkyl group, or a halogen; $n^1$ represents the number of the substituent $R^2$ in the range of 0–4; $R^3$ to $R^6$ each represents hydrogen, a lower alkyl group, or a lower halogenated alkyl group; and $Q^1$ represents any of lithium, sodium, potassium, MgCl, MgBr, or MgI.

6. The process of producing a bismuth compound as claimed in claim 4, wherein $R^1$ represents a methyl group; $R^2$ represents an alkyl group having 1–2 carbon atoms; $R^3$ and $R^4$ each represents hydrogen or an alkyl group having 1–2 carbon atoms; and $R^5$ and $R^6$ each represents an alkyl group having 1–2 carbon atoms.

7. The process of producing a bismuth compound as claimed in claim 6, wherein the monoaryl dihalogenated bismuth represented by the formula 2 is dichloro(2-(N,N-dimethylaminomethyl)phenyl)bismuth.

8. The process of producing a bismuth compound as claimed in claim 4, wherein the $R^1$-converting reagent is methyl magnesium bromide.

9. A process of producing a bismuth-containing film, which comprises subjecting the bismuth compound as claimed in claim 1, 2 or 3 as a precursor to chemical vapor deposition on a substrate to form a bismuth-containing film.

10. A bismuth compound represented by the following formula 5:

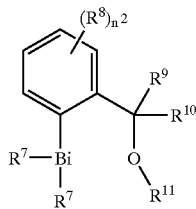

wherein $R^7$ represents a lower alkyl group; $R^8$ represents a lower alkyl group, a lower alkoxy group, a lower acyl group, a lower alkoxycarbonyl group, a lower halogenated alkyl group, or a halogen; $n^2$ represents the number of the substituent $R^8$ in the range of 0–4; and $R^9$ to $R^{11}$ each represents hydrogen, a lower alkyl group, or a lower halogenated alkyl group.

11. The bismuth compound as claimed in claim 10, wherein $R^7$ represents a methyl group; $R^8$ represents an alkyl group having 1–2 carbon atoms; $R^9$ and $R^{10}$ each represents hydrogen or an alkyl group having 1–2 carbon atoms; and $R^{11}$ represents an alkyl group having 1–2 carbon atoms.

12. The bismuth compound as claimed in claim 11, wherein $R^7$ represents a methyl group; $R^9$ and $R^{10}$ each represents hydrogen; $R^{11}$ represents a methyl group; and $n^2$ is 0.

13. A process of producing a bismuth compound as claimed in any one of claims 10 to 12, which comprises reacting a monoaryl dihalogenated bismuth represented by the following formula 6:

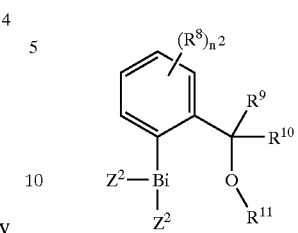

wherein $R^8$ represents a lower alkyl group, a lower alkoxy group, a lower acyl group, a lower alkoxycarbonyl group, a lower halogenated alkyl group, or a halogen; $n^2$ represents the number of the substituent $R^8$ in the range of 0–4; $R^9$ to $R^{11}$ each represents hydrogen, a lower alkyl group, or a lower halogenated alkyl group; and $Z^2$ represents a halogen, with an $R^7$-converting reagent, wherein $R^7$ represents a lower alkyl group.

14. A process of producing a bismuth compound as claimed in any one of claims 10 to 12, which comprises reacting a dialkyl monohalogenated bismuth represented by the following formula 7:

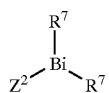

wherein $R^7$ represents a lower alkyl group; and $Z^2$ represents a halogen,
with an arylating reagent represented by the following formula 8:

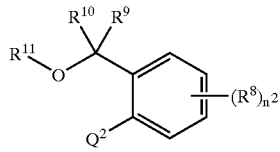

wherein $R^8$ represents a lower alkyl group, a lower alkoxy group, a lower acyl group, a lower alkoxycarbonyl group, a lower halogenated alkyl group, or a halogen; $n^2$ represents the number of the substituent $R^8$ in the range of 0–4; $R^9$ to $R^{11}$ each represents hydrogen, a lower alkyl group, or a lower halogenated alkyl group; and $Q^2$ represents any of lithium, sodium, potassium, MgCl, MgBr, or MgI.

15. The process of producing a bismuth compound as claimed in claim 13, wherein $R^7$ represents a methyl group; $R^8$ represents an alkyl group having 1–2 carbon atoms; $R^9$ and $R^{10}$ each represents hydrogen or an alkyl group having 1–2 carbon atoms; and $R^{11}$ represents an alkyl group having 1–2 carbon atoms.

16. The process of producing a bismuth compound as claimed in claim 15, wherein the monoaryl dihalogenated bismuth represented by the formula 6 is dichloro(2-(methoxymethyl)phenyl)bismuth.

17. The process of producing a bismuth compound as claimed in claim 13, wherein the $R^7$-converting reagent is methyl magnesium bromide.

18. A process of producing a bismuth-containing film, which comprises subjecting the bismuth compound as claimed in claim 10, 11 or 12 as a precursor to chemical vapor deposition on a substrate to form a bismuth-containing film.

19. A bismuth compound represented by the following formula 9:

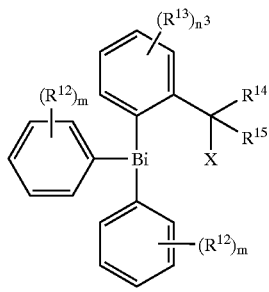

wherein $R^{12}$ and $R^{13}$ each represents a lower alkyl group, a lower alkoxy group, a lower acyl group, a lower alkoxycarbonyl group, a lower halogenated alkyl group, or a halogen; m represents the number of the substituent $R^{12}$ in the range of 0–5; $n^3$ represents the number of the substituent $R^{13}$ in the range of 0–4; $R^{14}$ and $R^{15}$ each represents hydrogen, a lower alkyl group, or a lower halogenated alkyl group; and X represents a substituent represented by the following formula 10 or 11:

wherein $R^{16}$ to $R^{18}$ each represents hydrogen, a lower alkyl group, or a lower halogenated alkyl group,
provided that the case (i) where X is represented by the formula 10, $R^{14}$ and $R^{15}$ each represents hydrogen, $R^{16}$ and $R^{17}$ each represents a methyl group, m is 1, $n^3$ is 0, and $R^{12}$ represents a 4-methyl group, a 4-methoxy group, or 4-chloro; and the case (ii) where X is represented by the formula 10, m and $n^3$ are each 0, $R^{15}$ represents hydrogen, $R^{16}$ and $R^{17}$ each represents a methyl group, and $R^{14}$ represents hydrogen or a methyl group are excluded.

20. The bismuth compound as claimed in claim 19, wherein $R^{12}$ and $R^{13}$ each represents an alkyl group having 1–2 carbon atoms or a halogenated alkyl group having 1–2 carbon atoms; $R^{14}$ and $R^{15}$ each represents hydrogen, an alkyl group having 1–2 carbon atoms, or a halogenated alkyl group having 1–2 carbon atoms; and $R^{16}$ to $R^{18}$ each represents an alkyl group having 1–2 carbon atoms, provided that the case (i) where X is represented by the formula 10, $R^{14}$ and $R^{15}$ each represents hydrogen, $R^{16}$ and $R^{17}$ each represents a methyl group, m is 1, $n^3$ is 0, and $R^{12}$ represents a 4-methyl group, a 4-methoxy group, or 4-chloro; and the case (ii) where X is represented by the formula 10, m and $n^3$ are each 0, $R^{15}$ represents hydrogen, $R^{16}$ and $R^{17}$ each represents a methyl group, and $R^{14}$ represents hydrogen or a methyl group are excluded.

21. The bismuth compound as claimed in claim 20, wherein X is represented by the formula 10, provided that the case (i) where $R^{14}$ and $R^{15}$ each represents hydrogen, $R^{16}$ and $R^{17}$ each represents a methyl group, m is 1, $n^3$ is 0, and $R^{12}$ represents a 4-methyl group, a 4-methoxy group, or 4-chloro; and the case (ii) where m and $n^3$ are each 0, $R^{15}$ represents hydrogen, $R^{16}$ and $R^{17}$ each represents a methyl group, and $R^{14}$ represents hydrogen or a methyl group are excluded.

22. The bismuth compound as claimed in claim 20, wherein X is represented by the formula 11.

23. The bismuth compound as claimed in claim 21, wherein $R^{12}$ represents a 3-methyl group; $R^{14}$ and $R^{15}$ each represents hydrogen; $R^{16}$ and $R^{17}$ each represents a methyl group; m is 1; and $n^3$ is 0.

24. The bismuth compound as claimed in claim 22, wherein $R^{14}$ and $R^{15}$ each represents hydrogen; $R^{18}$ represents a methyl group; and m and $n^3$ are each 0.

25. A process of producing a bismuth compound as claimed in any one of claims 19 to 24, which comprises reacting a diaryl monohalogenated bismuth represented by the following formula 12:

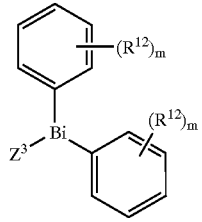

wherein $R^{12}$ represents a lower alkyl group, a lower alkoxy group, a lower acyl group, a lower alkoxycarbonyl group, a lower halogenated alkyl group, or a halogen; m represents the number of the substituent $R^{12}$ in the range of 0–5; and $Z^3$ represents a halogen,
with an arylating reagent represented by the following formula 13:

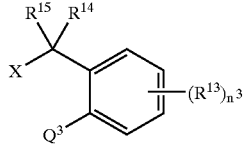

wherein $R^{13}$ represents a lower alkyl group, a lower alkoxy group, a lower acyl group, a lower alkoxycarbonyl group, a lower halogenated alkyl group, or a halogen; $R^{14}$ and $R^{15}$ each represents hydrogen, a lower alkyl group, or a lower halogenated alkyl group; $n^3$ represents the number of the substituent $R^{13}$ in the range of from 0 to 4; X represents a substituent represented by the following formula 10 or 11:

wherein $R^{16}$ to $R^{18}$ each represents hydrogen, a lower alkyl group, or a lower halogenated alkyl group; and $Q^3$ represents an alkali metal, MgCl, MgBr, or MgI,
provided that the case (i) where X is represented by the formula 10, $R^{14}$ and $R^{15}$ each represents hydrogen, $R^{16}$ and $R^{17}$ each represents a methyl group, m is 1, $n^3$ is 0, and $R^{12}$ represents a 4-methyl group, a 4-methoxy group, or 4-chloro; and the case (ii) where X is represented by the formula 10, m and $n^3$ are each 0, $R^{15}$ represents hydrogen, $R^{16}$ and $R^{17}$ each represents a methyl group, and $R^{14}$ represents hydrogen or a methyl group are excluded.

26. The process of producing a bismuth compound as claimed in claim 25, wherein $R^{12}$ and $R^{13}$ each represents an alkyl group having 1–2 carbon atoms or a halogenated alkyl group having 1–2 carbon atoms; $R^{14}$ and $R^{15}$ each represents hydrogen, an alkyl group having 1–2 carbon atoms, or a halogenated alkyl group having 1–2 carbon atoms; and $R^{16}$ to $R^{18}$ each represents an alkyl group having 1–2 carbon atoms, provided that the case (i) where X is represented by the formula 10, $R^{14}$ and $R^{15}$ each represents hydrogen, $R^{16}$ and $R^{17}$ each represents a methyl group, m is 1, $n^3$ is 0, and $R^{12}$ represents a 4-methyl group, a 4-methoxy group, or 4-chloro; and the case (ii) where X is represented by the formula 10, m and $n^3$ are each 0, $R^{15}$ represents hydrogen, $R^{16}$ and $R^{17}$ each represents a methyl group, and $R^{14}$ represents hydrogen or a methyl group are excluded.

27. The process of producing a bismuth compound as claimed in claim 26, wherein X is represented by the formula 10, provided that the case (i) where $R^{14}$ and $R^{15}$ each represents hydrogen, $R^{16}$ and $R^{17}$ each represents a methyl group, m is 1, $n^3$ is 0, and $R^{12}$ represents a 4-methyl group, a 4-methoxy group, or 4-chloro; and the case (ii) where m and $n^3$ are each 0, $R^{15}$ represents hydrogen, $R^{16}$ and $R^{17}$ each represents a methyl group, and $R^{14}$ represents hydrogen or a methyl group are excluded.

28. The process of producing a bismuth compound as claimed in claim 26, wherein X is represented by the formula 11.

29. The process of producing a bismuth compound as claimed in any one of claim 27, wherein the arylating reagent is 2-(N,N-dimethylaminomethyl)phenyllithium.

30. The process of producing a bismuth compound as claimed in claim 28, wherein the arylating reagent is 2-(methoxymethyl)phenyllithium.

31. The process of producing a bismuth compound as claimed in claim 27, wherein the diaryl monohalogenated bismuth is di(3-tolyl)monochlorobismuth, and the arylating reagent is 2-(N,N-dimethylaminomethyl)phenyllithium.

32. The process of producing a bismuth compound as claimed in claim 28, wherein the diaryl monohalogenated bismuth is diphenylmonochlorobismuth, and the arylating reagent is 2-(methoxymethyl)phenyllithium.

33. The process for producing a bismuth compound as claimed in claim 7, wherein the $R^1$-converting reagent is methyl magnesium bromide.

34. The process for producing a bismuth compound as claimed in claim 16, wherein the $R^7$-converting reagent is methyl magnesium bromide.

* * * * *